US011458299B2

(12) United States Patent
Cass et al.

(10) Patent No.: US 11,458,299 B2
(45) Date of Patent: Oct. 4, 2022

(54) STRAIN RELIEF COUPLER AND METHOD

(71) Applicant: Heraeus Medical Components LLC, St. Paul, MN (US)

(72) Inventors: Robert R. Cass, Minneapolis, MN (US); Paul Noffke, St. Paul, MN (US); Alan Carlson, St. Paul, MN (US)

(73) Assignee: Heraeus Medical Components LLC, St. Paul, MN (US)

( * ) Notice: Subject to any disclaimer, the term of this patent is extended or adjusted under 35 U.S.C. 154(b) by 60 days.

(21) Appl. No.: 16/787,352

(22) Filed: Feb. 11, 2020

(65) Prior Publication Data
US 2020/0179675 A1 Jun. 11, 2020

Related U.S. Application Data

(63) Continuation of application No. PCT/US2018/046476, filed on Aug. 13, 2018.
(Continued)

(51) Int. Cl.
*A61N 1/05* (2006.01)
*H01R 24/58* (2011.01)
(Continued)

(52) U.S. Cl.
CPC ............... *A61N 1/05* (2013.01); *A61N 1/048* (2013.01); *A61N 1/0488* (2013.01); *A61N 1/375* (2013.01);
(Continued)

(58) Field of Classification Search
CPC ...... A61N 1/05; A61N 1/0472; A61N 1/0476; A61N 1/048; A61N 1/0488; A61N 1/375; A61N 1/3752; H01R 43/24; H01R 24/58
See application file for complete search history.

(56) References Cited

U.S. PATENT DOCUMENTS 5,419,707 A * 5/1995 Kelley .................. H01R 31/00
439/21
8,644,953 B1 * 2/2014 Finley .................. A61N 1/0551
607/116
(Continued)

FOREIGN PATENT DOCUMENTS

WO 2005/042085 5/2005
WO 2013/062859 5/2013
WO 2013/062863 5/2013

OTHER PUBLICATIONS

Written Opinion and International Search Report dated Feb. 1, 2019 in PCT/US2018/046476.
(Continued)

*Primary Examiner* — Michael W Kahelin
*Assistant Examiner* — Pamela M. Bays
(74) *Attorney, Agent, or Firm* — Dicke, Billig & Czaja, PLLC

(57) ABSTRACT

A lead body for implantation includes a first set of conducting sections, a second set of conducting sections, a strain relief coupler having a axial length with a plurality of tines extending along the axial length and extending radially thereby defining a plurality of axially-extending channels, a plurality of joints located within the plurality of channels, each joint coupling one conducting section from the first set of conducting sections to one conducting section from the second set of conducting sections, and an outer layer at least partially surrounding the first and second set of conducting sections, the plurality of joints and the strain relief coupler.

9 Claims, 25 Drawing Sheets

Related U.S. Application Data

(60) Provisional application No. 62/544,563, filed on Aug. 11, 2017, provisional application No. 62/634,442, filed on Feb. 23, 2018, provisional application No. 62/643,793, filed on Mar. 16, 2018.

(51) Int. Cl.
*H01R 43/24* (2006.01)
*A61N 1/04* (2006.01)
*A61N 1/375* (2006.01)
*H01R 107/00* (2006.01)

(52) U.S. Cl.
CPC .......... *A61N 1/3752* (2013.01); *H01R 24/58* (2013.01); *H01R 43/24* (2013.01); *A61N 1/0472* (2013.01); *A61N 1/0476* (2013.01); *A61N 1/0534* (2013.01); *H01R 2107/00* (2013.01); *H01R 2201/12* (2013.01)

(56) References Cited

U.S. PATENT DOCUMENTS

| | | |
|---|---|---|
| 9,421,362 B2 | 8/2016 | Seeley |
| 10,076,657 B2 | 9/2018 | Oster et al. |
| 2005/0075554 A1* | 4/2005 | Bernhart ............. A61B 5/0536 600/373 |
| 2009/0222073 A1 | 9/2009 | Flowers et al. |
| 2011/0047795 A1 | 3/2011 | Turner et al. |
| 2011/0245887 A1* | 10/2011 | Klardie .................... A61N 1/05 607/2 |
| 2014/0316502 A1* | 10/2014 | Seeley ................. A61B 5/6867 607/116 |
| 2015/0031975 A1 | 1/2015 | Atalar et al. |
| 2015/0157851 A1 | 6/2015 | Sefkow et al. |
| 2015/0165217 A1 | 6/2015 | Hughes |
| 2015/0352366 A1* | 12/2015 | Seeley ................. H01R 13/504 607/116 |
| 2017/0106186 A1* | 4/2017 | Thompson ........... A61N 1/3752 |
| 2017/0373427 A1* | 12/2017 | Kompa ................. H01R 13/04 |
| 2020/0338335 A1 | 10/2020 | Cass et al. |

OTHER PUBLICATIONS

Non-Final Office Action in U.S. Appl. No. 16/638,212 dated Sep. 27, 2021.

\* cited by examiner

STRAIN RELIEF COUPLER AND METHOD

CROSS REFERENCE TO RELATED APPLICATION

This Utility patent application is a continuation of International Application Serial No. PCT/US2018/046476, filed Aug. 13, 2018, which claims the benefit of U.S. Patent Application Ser. No. 62/544,563, filed Aug. 11, 2017, U.S. Patent Application Ser. No. 62/634,442, filed Feb. 23, 2018 and U.S. Patent Application Ser. No. 62/643,793, filed Mar. 16, 2018; all of which are incorporated herein by reference.

BACKGROUND

This disclosure relates to a high-density lead body configured for use within the body of a mammal or human. In one case, segmented electrodes are provided on the lead body and configured for sensing and/or stimulation within a biological application. In some embodiments, ring electrodes are provided on the distal end of a lead for sensing and/or stimulation within a human body. The distal end of a lead is placed adjacent tissue that is to be sensed or stimulated and the ring electrodes either transmit or receive energy. Also, respective connectors or contacts, which are electrically coupled to the electrodes, are provided on the proximal end of a lead for plugging in to a medical device. In some cases, it is useful to have very discrete locations energized, and accordingly, use only a segment of a ring electrode, rather than the entire ring. Manufacturing discrete electrode segments can be difficult, particularly where multiple electrode segments are desired on a small diameter lead. For these and other reasons, there is a need for the present embodiments.

DETAILED DESCRIPTION

In the following Detailed Description, reference is made to the accompanying drawings, which form a part hereof, and in which is shown by way of illustration specific embodiments in which the embodiments may be practiced. In this regard, directional terminology, such as "top," "bottom," "front," "back," "leading," "trailing," etc., is used with reference to the orientation of the Figure(s) being described. Because components of the embodiments can be positioned in a number of different orientations, the directional terminology is used for purposes of illustration and is in no way limiting. It is to be understood that other embodiments may be utilized and structural or logical changes may be made without departing from the scope. The following detailed description, therefore, is not to be taken in a limiting sense, and the scope is defined by the appended claims.

Figure 1:
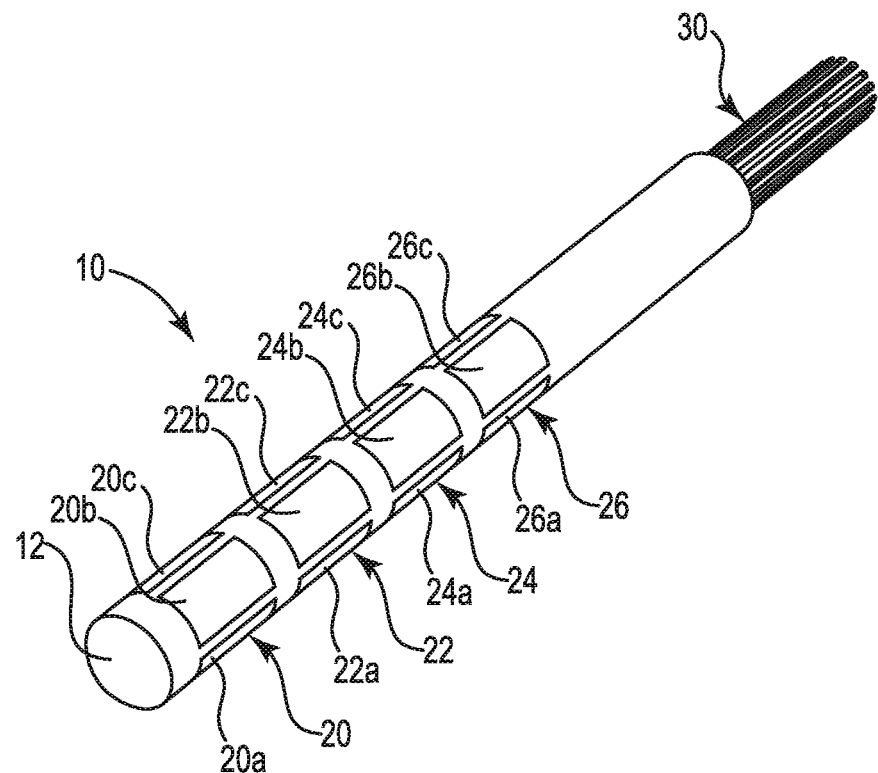
FIG. 1 illustrates a perspective view of a lead body with segmented electrodes in accordance with one embodiment.

FIG. 1 illustrates a perspective view of a lead body 10 in accordance with one embodiment. In one embodiment, lead 10 includes, adjacent its distal end 12, four electrodes 20, 22, 24, 26. In other embodiments, more or less electrodes may be included. In one embodiment, each of electrodes 20, 22, 24, 26 is segmented, such that each has a plurality of individually accessible electrode segments. In one embodiment, first electrode 20 includes first, second, third and fourth electrode segments 20a, 20b, 20c, and 20d; second electrode 22 includes first, second, third and fourth electrode segments 22a, 22b, 22c, and 22d; third electrode 24 includes first, second, third and fourth electrode segments 24a, 24b, 24c, and 24d; and fourth electrode 26 includes first, second, third and fourth electrode segments 26a, 26b, 26c, and 26d. In one embodiment, each electrode segment a/b/c/d of each electrode 20, 22, 24, 26 extend radially about the outer diameter of lead 10, and are each electrode segment a/b/c/d of each electrode 20, 22, 24, 26 are located along the same axial length of lead 10. Because the electrode segments are spaced radially about the circumference of lead 10, only some of the segments are visible in the side view of FIG. 1.

In various other embodiments, there can be any number of combinations of electrodes and electrode segments. For example, there can be two, three, four or five electrode segments for each of electrodes 20, 22, 24, 26. In some embodiments, some of the electrodes are single ring electrodes, without segmentation, while other of the electrodes are segmented in various combinations two, three, four or five or more segments (see, for example, FIGS. 15A and 15B). In some embodiments, less than four electrodes are used, and in others more than four are used.

In operation, lead 10 may be configured for use within a human body, such as within the vasculature. Once within a human body, each of electrode segments 20a/b/c/d, 22a/b/c/d, 24a/b/c/d, 26a/b/c/d may be used for directional stimulation or for positional feedback sensing. In one embodiment, rather than using a single ring electrode that spans the entire 360° circumference of the lead, lead 10 includes electrode segments 20a/b/c/d, 22a/b/c/d, 24a/b/c/d, 26a/b/c/d, which only span a portion of the circumference of lead 10 (for example, 180°, 90° degrees or less), such that directional stimulation or positional feedback sensing can be much more precisely controlled relative to a given target within the human body.

A plurality of conducting sections 30 are illustrated extend from lead 10. Each electrode segment 20a/b/c/d, 22a/b/c/d, 24a/b/c/d, 26a/b/c/d has a single corresponding conducting section within the plurality of conducting sections 30, and each are electrically isolated from each other. The plurality of conducting sections 30 are available at the proximal end of lead 10 such that each electrode segment 20a/b/c/d, 22a/b/c/d, 24a/b/c/d, 26a/b/c/d is electrically accessible at the proximal end of lead 10 via one conducting section of the plurality of conducting sections 30.

Lead body 10 in accordance with embodiments described herein, allow for the manufacture of leads having increased density of electrode segments. Increased density of electrode segments is useful in a variety of applications. For example, lead 10 can be used in deep brain stimulation (DBS), in which lead 10 delivers electrical pulses into one or several specific sites within the brain of a patient to treat various neurological disorders, such as chronic pain, tremors, Parkinson's disease, dystonia, epilepsy, depression, obsessive-compulsive disorder, and other disorders. In other applications, lead 10 may be configured for spinal cord stimulation, peripheral nerve stimulation, dorsal root stimulation, cortical stimulation, ablation therapies, cardiac rhythm management leads, various catheter configurations for sensing, and various other therapies where directional sensing or stimulation are needed.

Figure 2:
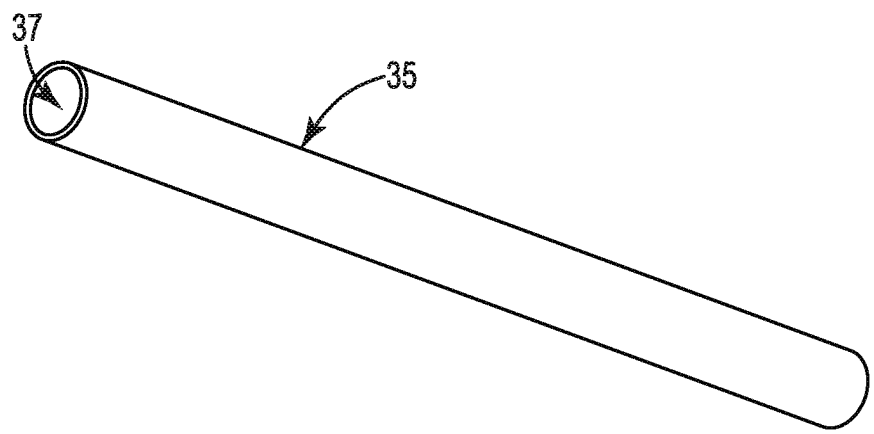
FIG. 2 illustrates a perspective view of hypotube for manufacturing a lead body in accordance with one embodiment.

In one embodiment, the manufacture of lead 10 begins with a hypotube 35, such as illustrated in FIG. 2. Hypotube 35 is a tube that has an open center lumen 37 and also has a very small micro outside diameter, for example, as small as 0.040 or 0.005 inches. Hypotubes 35 can be any of a variety of materials, and in one embodiment is stainless steel. In one embodiment, hypotube 35 is sectioned into a plurality of conducting sections via any number of sectioning methods. In one embodiment, hypotube 35 is cut into sections using a laser. In another embodiment, it is chemically etched into sections. Other methods are also possible on accordance with other embodiments.

Figure 3A:
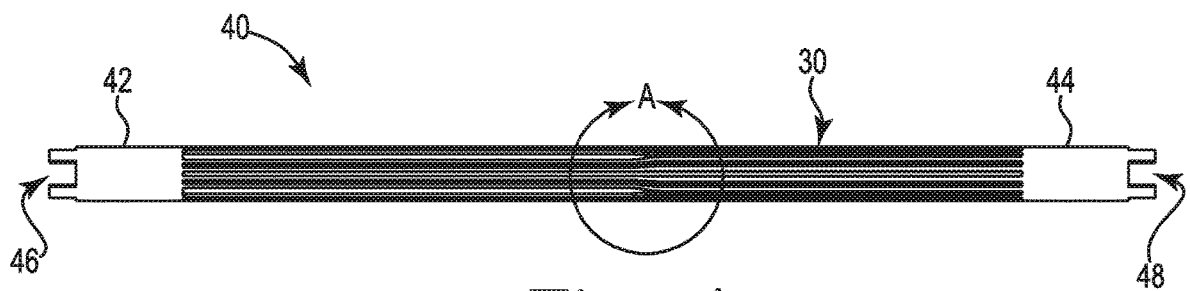
FIG. 3A illustrates a side view of a sectioned hypotube for a lead body in accordance with one embodiment.

Sectioned hypotube 40 illustrated in FIG. 3A is a hypotube, such as hypotube 35, which has been sectioned to form a plurality of conducting sections 30. In one embodiment, first and second ends 42 and 44 of sectioned hypotube 40 remain solid tube portions, and are not sectioned. Between first and second ends 42 and 44, a plurality of conducting sections 30 are formed by the removal of material from hypotube 35, for example, by laser cutting. The number of conducting sections within plurality of conducting sections 30 can be varied such that one conducting section is provided for each segment of a segmented electrode, or such that one conducting section is provided for each ring electrode. The conducting sections are all formed in the cylindrical diameter of the hypotube 35, such that the inner lumen 37 of sectioned hypotube 40 extends within the plurality of conducting sections 30, and such that the outer profile of each conducting section retains the cylindrical diameter of hypotube 35. In one embodiment, first and second ends 42 and 44 are respectively provided with first and second keys 46 and 48, which can be useful in the assembly of lead 10 as will be discussed further below.

Figure 3B:
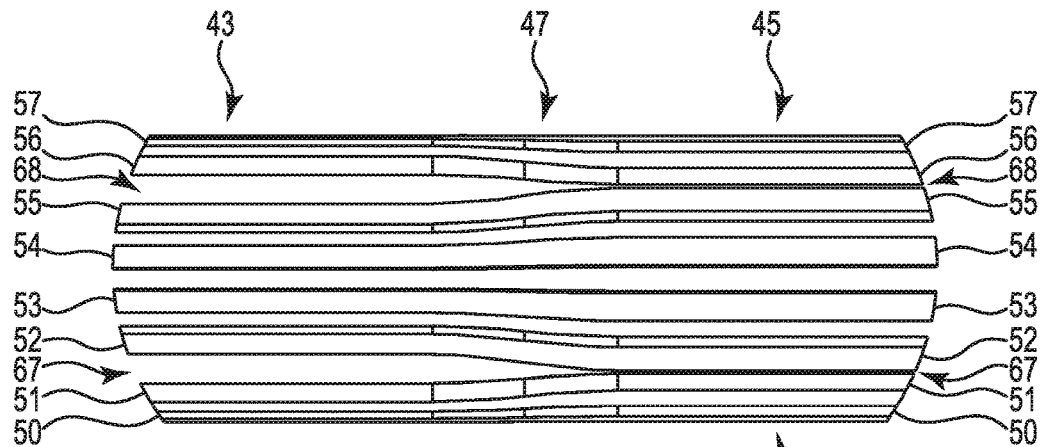
FIG. 3B illustrates an exploded view of a portion of the sectioned hypotube illustrated in FIG. 3A.
Figure 3C:
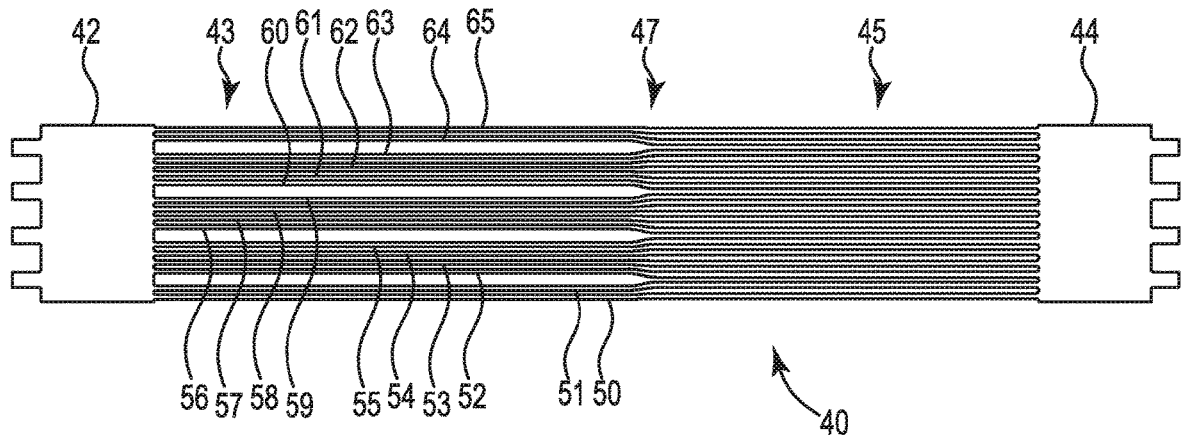
FIG. 3C illustrates a top view of a flattened sectioned hypotube illustrated in FIG. 3A.

FIG. 3B illustrates a more detailed portion A of sectioned hypotube 40 from FIG. 3A. In one embodiment, the plurality of conducting sections 30 includes 16 individual conducting sections 50-66. Because the conducting sections 50-66 are arranged radially about the circumference of sectioned hypotube 40, only a portion, that is, first through seventh conducting sections 50-57, are visible in the side view of sectioned hypotube 40 in FIGS. 3A and 3B. Accordingly, FIG. 3C illustrates the sectioned hypotube 40 illustrated in FIG. 3A, but in a flattened state. In actual use, sectioned hypotube 40 is not flattened and remains in a cylindrical or tube shape, but is illustrated in FIG. 3C as flattened simply so that all 16 conducting sections 50-66 are visible in a two-dimensional drawing.

In one embodiment, certain of the conducting sections among the plurality of conducting sections 30 are grouped closer together than are other segments. This can be useful when there are many conducting sections and many corresponding segmented electrodes, as will be further discussed below. In one embodiment, certain of the conducting sections are grouped closer together in a first axial section 43, while in a second axial section 45, each of the conducting sections are generally equally spaced around the circumference of sectioned hypotube 40. Accordingly, some of the conducting sections jog slightly in jog section 47. For example, in one embodiment, FIG. 3B illustrates that conducting sections 52-55 are grouped closer together in first axial section 43, such that the space 68 between conducting sections 55 and 56 is larger in first axial section 43 than it is in second axial section 45. Similarly, the space 67 between conducting sections 51 and 52 is larger in first axial section 43 than it is in second axial section 45. These larger spaces in between groups of conducting sections in the first axial section 43 are also visible in FIG. 3C, as is the generally equally spacing between the conducting sections in the second axial section 45. Because conducting sections 50-66 are formed by sectioning hypotube 30, their respective width and the spacing between them is readily controlled and adjusted based on the need for any particular application.

Figure 4A:
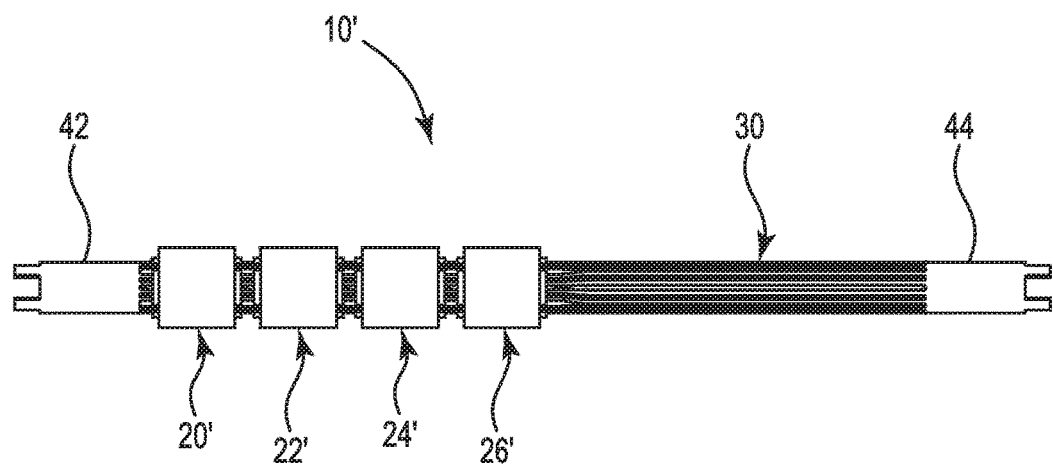
FIG. 4A illustrates a side view of an electrode assembly for a lead body in accordance with one embodiment.
Figure 4B:
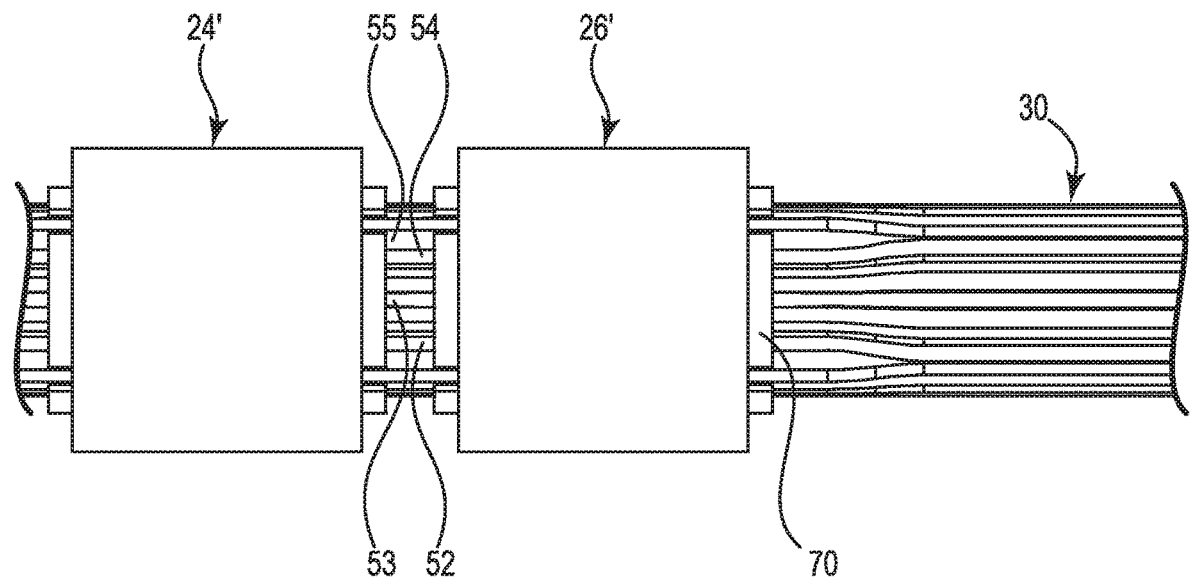
FIG. 4B illustrates an enlarged side view of a portion of an electrode assembly for a lead body in accordance with one embodiment.

FIGS. 4A and 4B illustrates electrode assembly 10' for a lead in accordance with one embodiment. In one embodiment, non-ground electrodes 20', 22', 24', 26' are placed over sectioned hypotube 40 to form electrode assembly 10'. In one embodiment, non-ground electrodes 20', 22', 24', 26' are placed over first axial section 43, where conducting sections are grouped in order to facilitate coupling conducting sections 50-66 to specific locations of non-ground electrodes 20', 22', 24', 26'. Conducting sections 52, 53, 54, 55 are illustrated extending through non-ground electrode 26' and into non-ground electrode 24'.

Figure 5A:
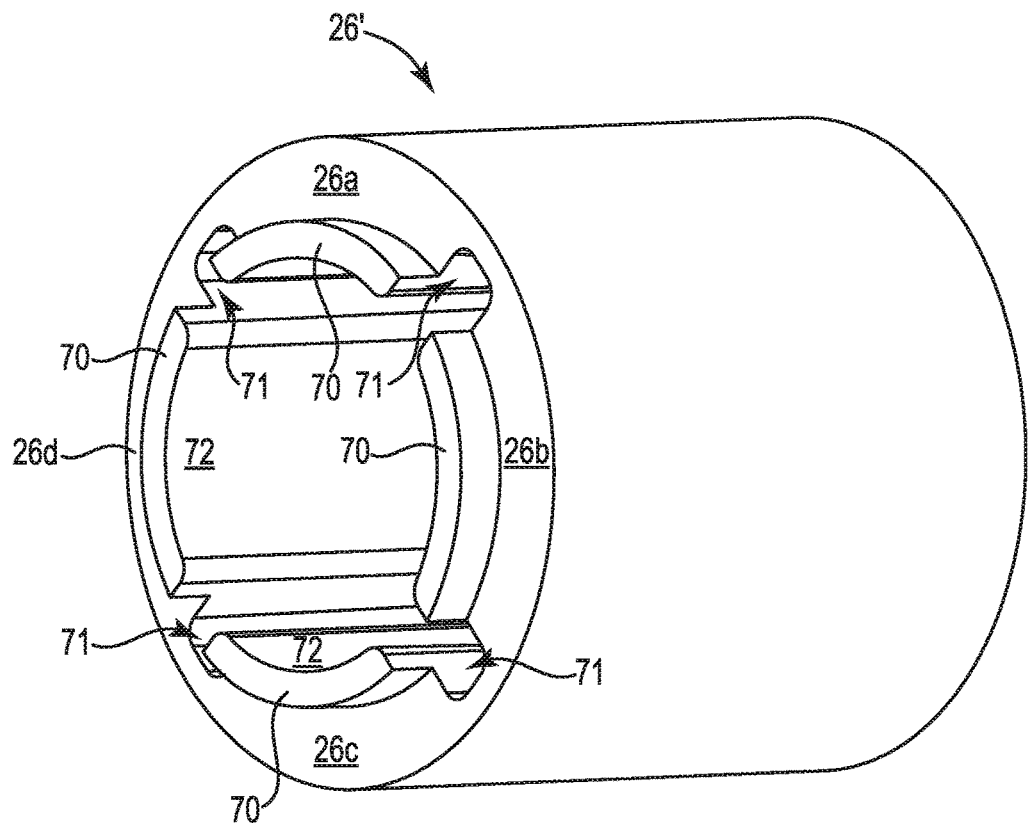
FIG. 5A illustrates a perspective view of a non-ground electrode for an electrode assembly for a lead body in accordance with one embodiment.
Figure 5B:
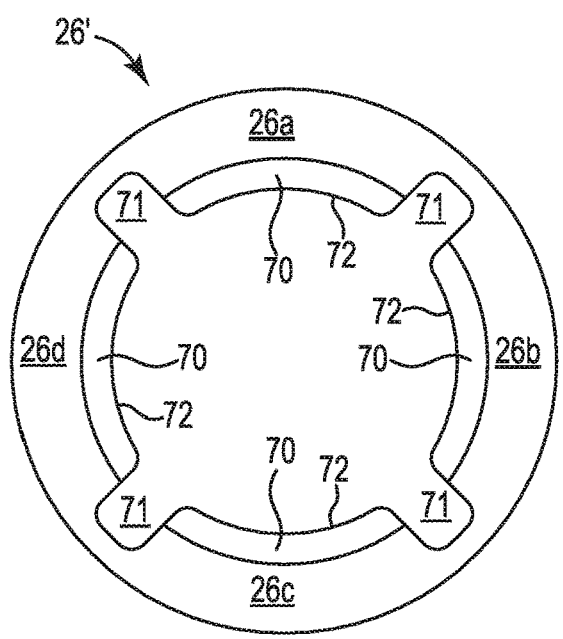
FIG. 5B illustrates an end view of a non-ground electrode for an electrode assembly for a lead body in accordance with one embodiment.

FIGS. 5A and 5B illustrate non-ground electrode 26' from electrode assembly 10' for manufacturing a lead in accordance with one embodiment. In one embodiment, non-ground electrode 26' is configured to provide four electrode segments 26a, 26b, 26c, and 26d for lead 10, after a centerless grinding process is performed on it.

In one embodiment, non-ground electrode 26' is provided with openings 71, which are equally spaced apart radially, separated by 90°. As such, when non-ground electrode 26' is subject to a centerless grinding process, openings 71 are exposed in the outer profile such that first through fourth electrode segments 26a, 26b, 26c, 26d are defined, and each are electrically isolated from the other by opening 71 (this is illustrated, for example, in FIGS. 8A and 8B). In other embodiments where more or less electrode segments are used, the number of openings and spacing thereof is appropriately adjusted. For example, if three electrode segments are used, three opening are provided spaced apart by 120°. Also, in some embodiments, it may be desirable to have one larger electrode segment with two smaller segments (see, for example, FIG. 16). In one such embodiment, two openings can be separated by 120°, while the others are separated by 90°. Any number of embodiments are possible. In one embodiment, the number of conducting sections provided matches the number of electrode segments so that each can be independently accessed.

In one embodiment, each electrode segment 26a, 26b, 26c, 26d has a generally cylindrical inner surface 72 to which an individual conducting section from the plurality of conducting sections 30 can be attached. In one embodiment, one conducting section from the plurality of conducting sections 30 is welded to one inner surface 72 of an electrode segment for all the electrodes. In this way, each electrode segment is electrically coupled to one, and only one, of the plurality of conducting sections 30. In one embodiment, each conducting section is cut from its connection to first end 42 as it is welded to inner surface 72 of the respective electrode. Once each of the plurality of conducting sections 30 is welded to an inner surface 72, first end 42 will be entirely removed from sectioned hypotube 40 (as illustrated, for example, in FIG. 6).

In one embodiment, each electrode segment is further provided with a retention tab 70. In one embodiment, this feature assists securing the segmented electrode within lead 10 after it is fully assembled. Retention feature 70 is configured to remain embedded within a molded portion of lead 10 after electrode 26' is ground.

Figure 6:
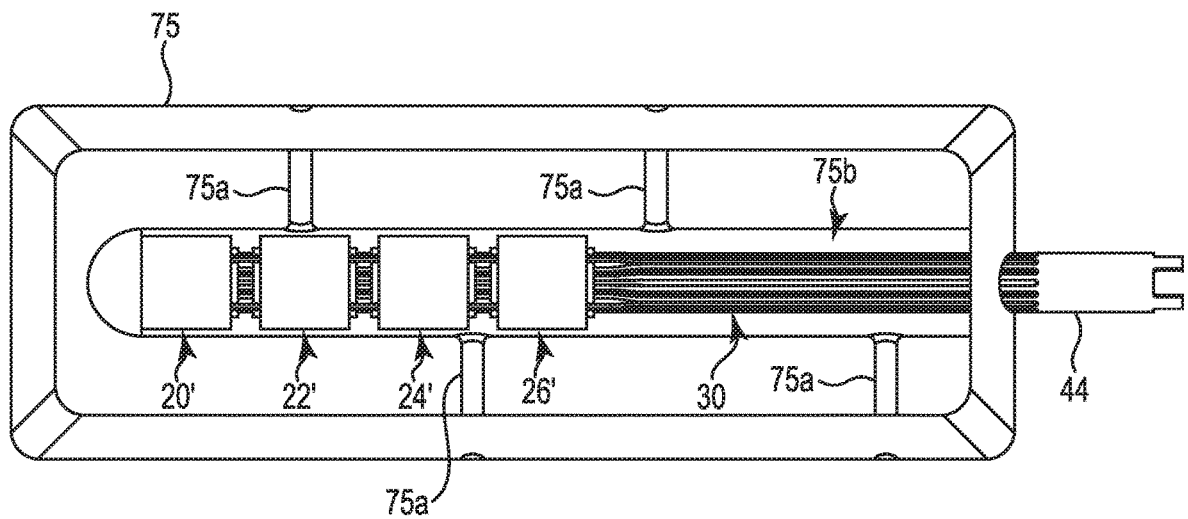
FIG. 6 illustrates a top view of an electrode assembly for a lead body in a mold cavity in accordance with one embodiment.

FIG. 6 illustrates electrode assembly 10' for lead 10 placed within an injection mold 75 in accordance with one embodiment. Injection mold 75 includes mold cavity 75b, in which electrode assembly 10' is placed, and mold gates 75a. Once mold cavity 75b is closed against its mirror image cavity (not illustrated), molding material, such as thermoplastic or elastomer insulation, is flowed into cavity 75b via mold gates 75a. The mold material fills all spaces within electrode assembly 10', including filing around the combination of non-ground electrodes 20', 22', 24', 26' and plurality of conducting sections 50-65. In one embodiment, a mandrel or core pin is inserted into the center lumen of electrode assembly 10' before placing it into mold 75 in order to prevent mold material from flowing into the assembly center and maintaining its central lumen.

In one embodiment, first end 42 of sectioned hypotube 40 is cut off as each of conducting sections 50-65 are welded to the respective inner surface 72 of the electrode segment. Second end 44, however, can be left attached while electrode assembly 10' is overmolded so that the plurality of conducting sections 30 are supported at one end by the weld to the electrode and at the other end by second end 44, such that they are not significantly disturbed by the force with which the mold material enters cavity 75b. Also, keys 48 at second end 44 may be useful for registering assembly 10' properly within mold cavity 75b.

Figure 7A:
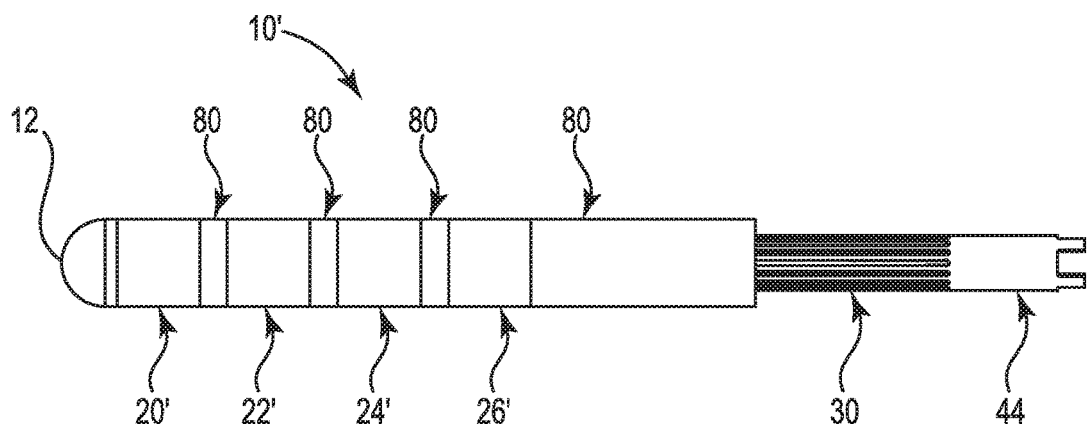
FIG. 7A illustrates a side view of an electrode assembly after molding and before centerless grinding in accordance with one embodiment.

FIG. 7A illustrates a side view of the electrode assembly 10' after the mold material 80 solidifies. Mold material 80 fills the voids between each of non-ground electrodes 20', 22', 24', 26', such that each is electrically isolated from each other by the insulative molding material 80. The molding material 80 also flows over a portion of the plurality of conducting sections 30, such that they are surrounded and firmly secured with the molding material, and electrically isolated from each other.

Figure 7B:
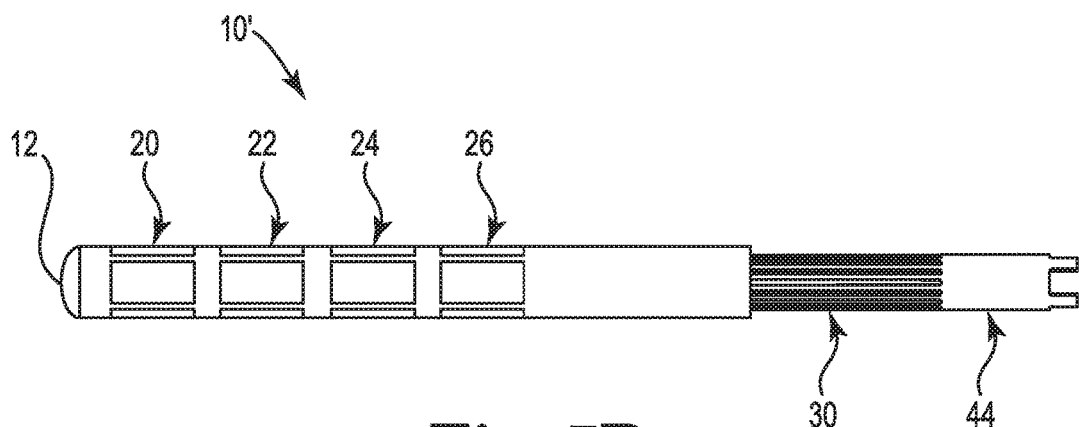
FIG. 7B illustrates a side view of an electrode assembly after centerless grinding in accordance with one embodiment.

The electrode assembly 10' illustrated in FIG. 7A is then subjected to a centerless grinding process that results in electrode assembly 10' illustrated in FIG. 7B. As is illustrated, each of non-ground electrodes 20', 22', 24', 26' is ground from the outside toward the inside such that openings 71 are exposed to the outer profile thereby defining the individual electrode segments of electrodes 20, 22, 24, 26. Finally, once second end 44 is removed, lead body 10, illustrated in FIG. 1, is provided. Each one of the plurality of conducting sections 30 extending from the proximal end of the lead body couple to and correspond with one electrode segment on the lead 10. As such, each conducting section can be coupled to a wire that can extend through a catheter and can be used to sense at, or send a signal to, one electrode segment on the lead 10.

In one embodiment, the centerless grinding process can be done before the electrode assembly 10' is molded, and in another embodiment, the centerless grinding process is done after the assembly 10' is molded. FIGS. 7A and 7B illustrate the later embodiment.

Figure 8A:
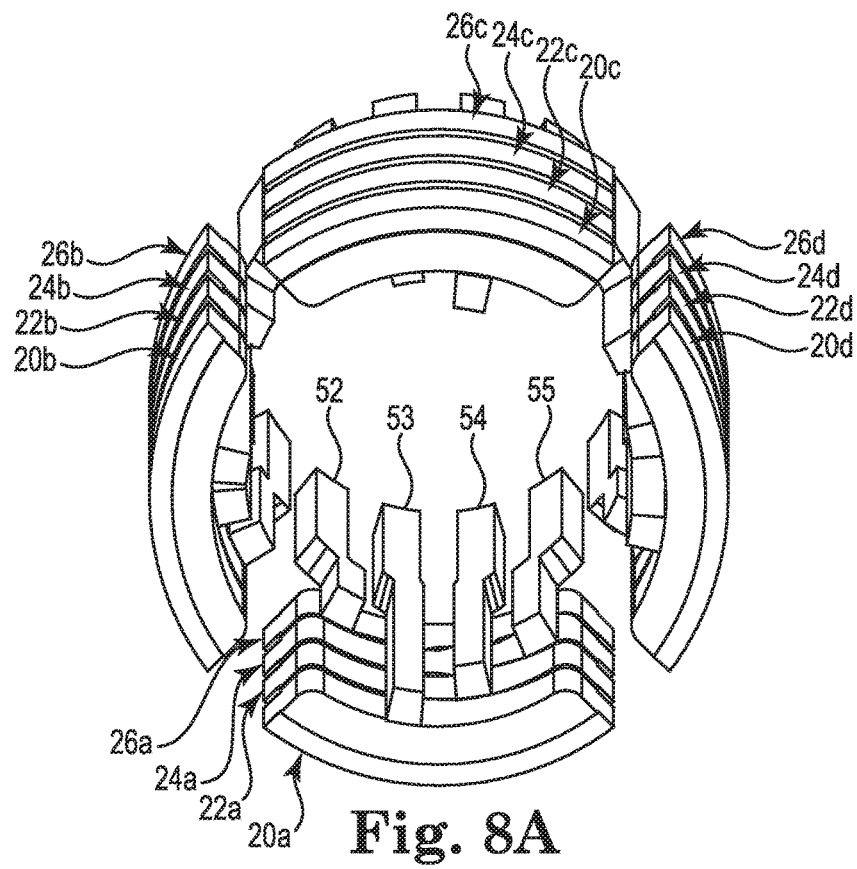
FIG. 8A illustrates a perspective partial end view, with portions removed, of a lead body with in accordance with one embodiment.

FIG. 8A illustrate a partial portion of lead 10, with portions such as the insulative molding material 80 removed, in order to further illustrate the coupling of conducting sections 50-65 to electrodes 20, 22, 24, 26. In one embodiment, sectioned hypotube 40 includes 16 conducting sections 50-65 and lead 10 includes four electrodes 20, 22, 24, 26, each having four electrode segments a/b/c/d. As previously discussed, in one embodiment, certain of conducting sections 50-65 are grouped or spaced closer together in the portion on lead 10 where the conducting sections 50-65 attach to electrodes 20, 22, 24, 26.

Figure 8B:
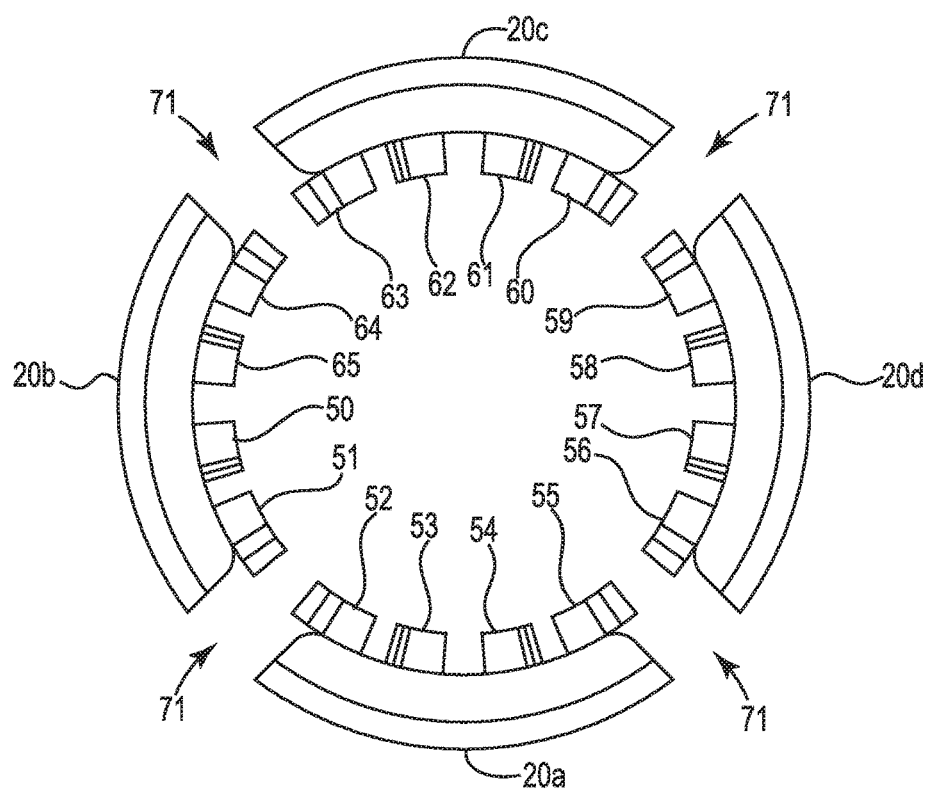
FIG. 8B illustrates a partial end view, with portions removed, of a lead body with in accordance with one embodiment.

As illustrated in FIGS. 8A and 8B, conducting sections 53, 54, 55, 52 are grouped closer together and respectively attach to electrode segments 20a, 22a, 24a, 26a; conducting sections 65, 50, 51, 64 are grouped closer together and respectively attach to electrode segments 20b, 22b, 24b, 26b; conducting sections 61, 62, 63, 60 are grouped closer together and respectively attach to electrode segments 20c, 22c, 24c, 26c; and conducting sections 57, 58, 59, 56 are grouped closer together and respectively attach to electrode segments 20d, 22d, 24d, 26d.

In one embodiment, grouping conducting sections together immediately adjacent the inner surface of the electrode segments allows larger spaces to be left between adjacent conducting sections adjacent openings 71. This allows positioning of each conducting section on an inner surface of an electrode segment and away from opening 71 between adjacent electrode segments. If electrode segments are placed too close to opening 71, there is some risk that the conducting section can be affected by the centerless grinding process, and possibly decoupled from the electrode segment.

In one embodiment, those conducting sections of sectioned hypotube 40 that extend all the way to the most distal end 12, that is, such as electrode 20, are longer than those that only extend to the relatively more proximally located, that is, such as electrode 26. In one embodiment, those longer conducting sections are attached to the respective electrode segments toward its radial center, and away from opening 71. In FIG. 8A, conducting sections 53 and 54, which extend out to electrodes 20 and 22, are relatively longer than conducting sections 52 and 55, which extend only to electrodes 26 and 24. As such, conducting sections 53 and 54 are located radially in between conducting sections 52 and 55. In this way, when all the conducting sections 50-65 are subjected to pressures, such as during the injection molding process, those that are longer tend to get moved more with the pressure. In one embodiment, locating the longer segments away from the openings 71 helps prevent them from moving into the openings 71 so that they are not later affected by the centerless grinding process.

Figure 9:
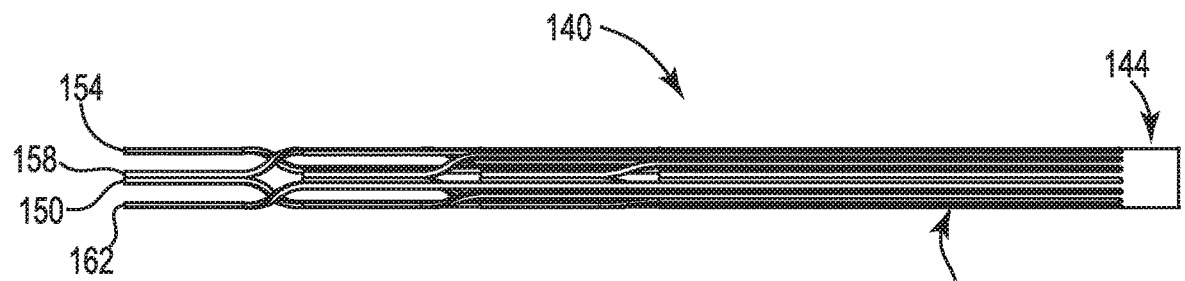
FIG. 9 illustrates a side view of a sectioned hypotube for a lead body in accordance with one embodiment.

Other configurations for sectioned hypotube 40 are also possible within other embodiments of lead body 10. For example, sectioned hypotube 140 is illustrated in FIG. 9. Similar to sectioned hypotube 40, sectioned hypotube 140 begins as a hypotube, such as hypotube 35 in FIG. 2, and is sectioned to form a plurality of conducting sections 130. In one embodiment, end 144 remains a solid tube portion, and is not sectioned. Sectioned hypotube 140 is configured to be coupled to non-ground electrodes, overmolded, and subjected to a centerless grinding process, as described above with respect to sectioned hypotube 40.

Adjacent to end 144, a plurality of conducting sections 130 are formed by the removal of material from hypotube 35, for example, by laser cutting. As is the case for sectioned hypotube 40 above, the number of conducting sections within plurality of conducting sections 130 can be varied such that one conducting section is provided for each segment of a segmented electrode, or such that one conducting section is provided for each ring electrode.

In one embodiment, sectioned hypotube 140 is laser cut, or otherwise sectioned, such that the plurality of conducting sections 130 have a slight spiral pattern in order to facilitate connection to the electrodes. As with sectioned hypotube 40, sectioned hypotube 140 is configured to have non-ground electrodes placed adjacent the distal end. In one embodiment, four non-ground electrodes are used (such as 120', 122', 124', 126' in FIG. 11), but any number of electrodes may be used in other embodiments. Conducting sections

150, 154, 158 and 162 are illustrated at the most distal end on sectioned hypotube 140 in FIG. 9, and are positioned, with a spiral pattern, to be respectively coupled to four segments of a segmented electrode.

Figure 10:
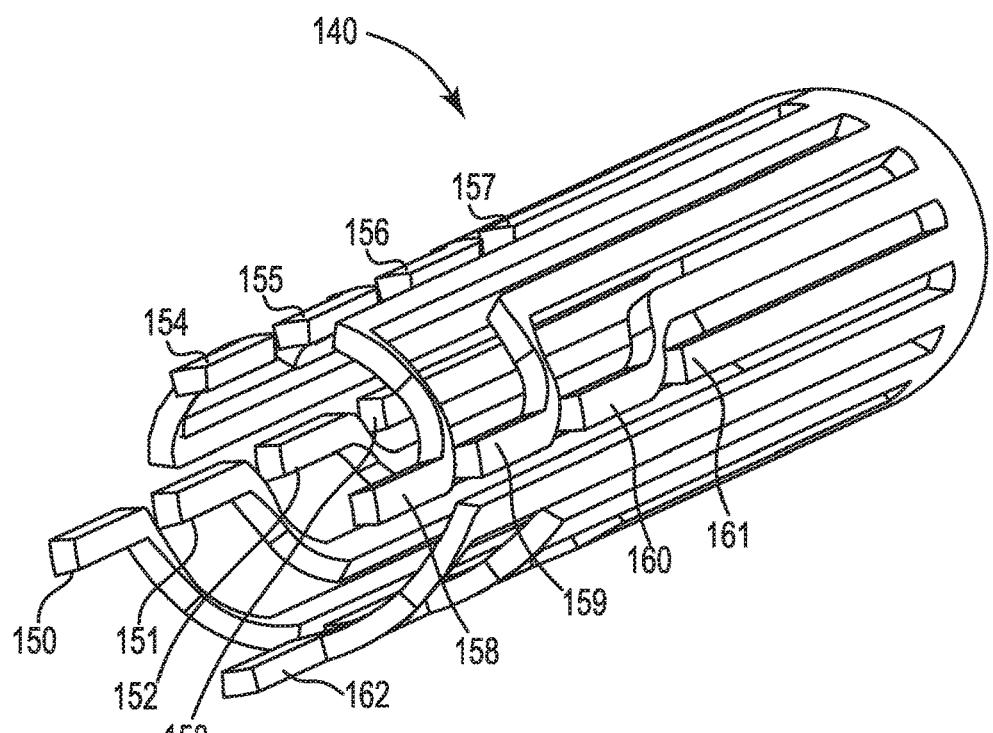
FIG. 10 illustrates a perspective view of a sectioned hypotube for a lead body in accordance with one embodiment.

FIG. 10 illustrates a perspective view of sectioned hypotube 140, such that its spiraled pattern is even more evident. For example, conducting sections 150, 151, 152 and 153 are slightly spiraled such that they align axially and can be readily coupled respectively to four axially aligned electrode segments. Similarly, conducting sections 154, 155, 156 and 157 are similarly aligned, as are conducting sections 158, 159, 160 and 161. Finally, although not fully visible in FIG. 10, conducting sections 162, 163, 164 and 165 are similarly aligned.

Figure 11:
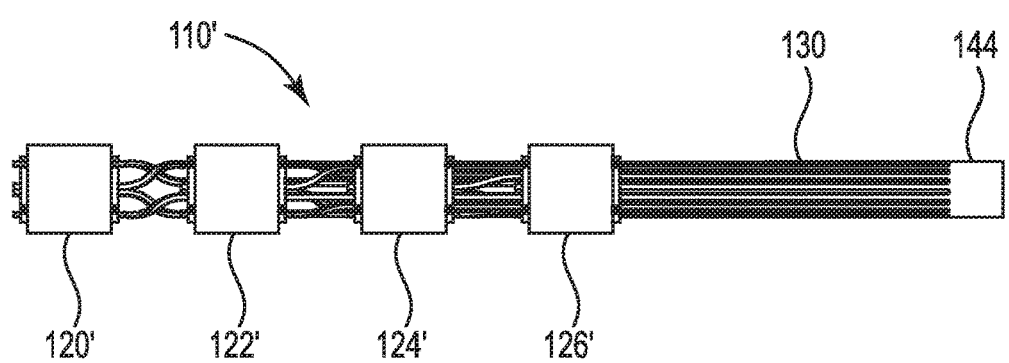
FIG. 11 illustrates a side view of an electrode assembly for a lead body in accordance with one embodiment.

FIG. 11 illustrates non-ground electrodes 120', 122', 124', 126' coupled to sectioned hypotube 140 to form electrode assembly 110'. In one embodiment, non-ground electrodes 120', 122', 124', 126' are placed over the proximal axial section, where conducting sections are spiraled in order to facilitate coupling conducting sections to specific locations of non-ground electrodes 120', 122', 124', 126'.

Figure 12:
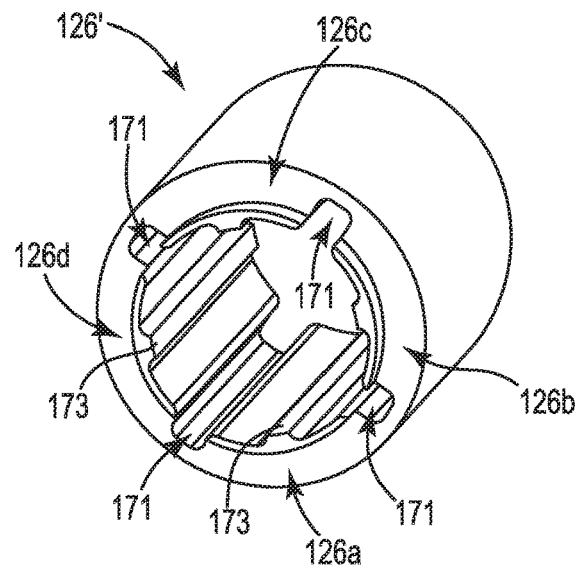
FIG. 12 illustrates a perspective view of a non-ground electrode for an electrode assembly for a lead body in accordance with one embodiment.

FIG. 12 illustrates non-ground electrode 126' from electrode assembly 110' for manufacturing a lead in accordance with one embodiment. In one embodiment, non-ground electrode 126' is configured to provide four electrode segments 126a, 126b, 126c, and 126d for lead 10, after a centerless grinding process is performed on it.

In one embodiment, non-ground electrode 126' is provided with openings 171, which are equally spaced apart radially, separated by 90°. As such, when non-ground electrode 126' is subject to a centerless grinding process, openings 171 are exposed in the outer profile such that first through fourth electrode segments 126a, 126b, 126c, 126d are defined, and each are electrically isolated from the other by opening 171. In other embodiments, where more or less electrode segments are used, the number of openings and spacing thereof is appropriately adjusted, as has been discussed previously.

In one embodiment, each electrode segment 126a, 126b, 126c, 126d has an inner surface with a raised ridge 173, to which an individual conducting section from the plurality of conducting sections 130 can be attached. In one embodiment, one conducting section from the plurality of conducting sections 130 is laser welded to one raised ridge 173 of an electrode segment for all the electrodes. In this way, each electrode segment is electrically coupled to one of the plurality of conducting sections 130.

In one embodiment, the outer diameter of the sectioned hypotube 140, and thus of the plurality of conducting sections 130 is slightly smaller than diameter of the inner surface of the non-ground electrodes 120', 122', 124', 126'. In this way, the plurality of conducting sections 130 are easily inserted into the electrodes. The raised ridge 173 on the inner surface of the non-ground electrodes 120', 122', 124', 126' then extends out from the inner surface to meet up with the outer diameter of the plurality of conducting sections 130 such that one conducting section is readily weldable to the raised ridge 173.

Once electrode assembly 110' is formed and each of the plurality of conducting sections 130 is welded to one raised ridge 173 of an electrode segment, assembly 110 is placed in a mold cavity, such as mold cavity 75a in FIG. 6. Mold material is formed over electrode assembly 110' in the same way described above for electrode assembly 10'. Similarly, the mold material fills all spaces within electrode assembly 110', including filling around the combination of non-ground electrodes 120', 122, 124', 126' and plurality of conducting sections 130.

After electrode assembly 110' is removed from the mold, it appears substantially identical to that represented in FIG. 7A, with mold material filling the voids between each of non-ground electrodes 120', 122', 124', 126', such that each is electrically isolated from each other by the insulative molding material. The molding material also flows over a portion of the plurality of conducting sections 130, such that they are surrounded and firmly secured with the molding material, and electrically isolated from each other.

The electrode assembly 110' is then subjected to a centerless grinding process, and once second end 144 is removed, lead body 10, illustrated in FIG. 1, is provided. Each one of the plurality of conducting sections 30/130 extending from the proximal end of the lead body couple to and correspond with one unique electrode segment on the lead 10. As such, each conducting section can be coupled to a wire that can extend through a catheter and can be used to sense at or send a signal to one electrode segment on the lead 10.

Figure 13:
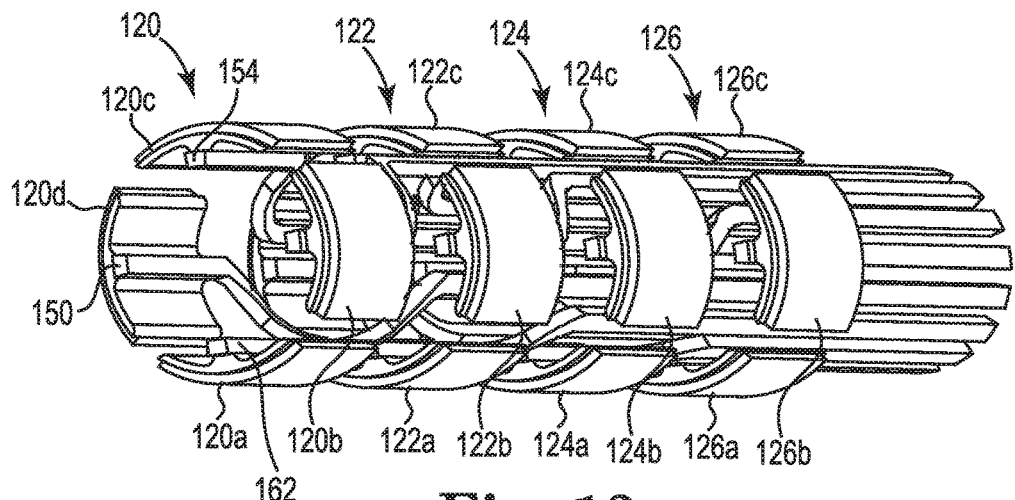
FIG. 13 illustrates a perspective partial view, with portions removed, of a lead body with in accordance with one embodiment.

FIG. 13 illustrate a partial portion of lead 10, with portions such as the insulative molding material removed, in order to further illustrate the coupling of conducting sections 150-165 to electrodes 120, 122, 124, 126. In one embodiment, sectioned hypotube 140 includes 16 conducting sections 150-165 and lead 10 includes four electrodes 120, 122, 124, 126, each having four electrode segments a/b/c/d. As previously discussed, in one embodiment, certain of conducting sections 50-65 are spiraled in the portion on lead 10 where the conducting sections 150-165 attach to electrodes 120, 122, 124, 126.

As illustrated in FIG. 13, the overall spiral shape of the conducting sections locates conducting section 150 substantially in the center of electrode segment 120d, locates conducting section 154 substantially in the center of electrode segment 120c, locates conducting section 158 substantially in the center of electrode segment 120b, and locates conducting section 162 substantially in the center of electrode segment 120a, where each are respectively welded to the raised ridge 173 on the inner surface. The remaining conducting sections are similarly attached to electrode segments a/b/c/d of electrodes 120, 122, 124, 126.

Manufacturing lead body 10 to produce segmented electrodes using a sectioned hypotube achieves an array on a small diameter lead. In one embodiment, using a laser cut hypotube creates sixteen discrete channels, which is not easily obtained with conventional techniques. Typically, segmented electrodes route wires directly up to the electrode segments, and wire management and support becomes prohibitive from a manufacturing perspective. Because the sectioned hypotube supports each conductive section with first and/or second unsectioned ends, it does not require the same wire management and external supports.

Furthermore, in one embodiment, the use of sectioned hypotubes also provides weld spots that are visible for inspection. As illustrated, for example, in FIGS. 8A, 8B and 13, the weld of the conducting sections of the sectioned hypotube to the electrode segments are readily visible and easily be inspected. Traditional weld spots are hidden on the inner diameter of the electrode and cannot be easily viewed or inspected.

In addition, the extension of the sectioned hypotube beyond the overmolded section of lead 10, facilitate relatively easy connection to other conducting sections or wire conductors that can then extend further toward the proximal end of the lead. Each such wire is then independently conductively coupled to one electrode segment out at the distal end of the lead.

In one embodiment, a parylene coating or similar insulator material is formed over the electrodes and over the sectioned hypotube prior to joining electrodes and sectioned hypotube. This further ensures that each of the conducting sections and associated electrode segments are insulated relative to each other and to lead. The parylene coating is ground off the electrodes after assembly and is effectively removed during the welding of the conducting sections to the associated electrode segments such that there is an electrical coupling of the conducting sections to the electrode segments where they have been welded together.

In one embodiment, the use of sectioned hypotubes achieves decreased outer diameters of lead 10. In one embodiment, a lead with a sectioned hypotube is sized with an outer diameter of 0.031 inches, making it appropriate for small animal or pediatric applications. In one embodiment, the number of conducting sections that can be included within a lead body is a function of the OD of each of the conducting sections. In various embodiments, the following Table 1 illustrates achievable conducting section OD with associated achievable lead body overall OD and overall number of conducting sections:

TABLE 1

| | | Achievable Lead Diameter | |
|---|---|---|---|
| | | 8 Channel | 16 Channel |
| Conducting Section OD (in) | .001" | .021" | .031" |
| | .003" | .031" | .051" |
| | .005" | .041" | .064" |
| | .010" | .064" | .103" |

As illustrated, when coupling a conducting section that has an OD of 0.001 inches to an electrode in a lead body, as many as 8 overall conducting sections can be included within a lead body that has an OD of 0.021 inches, and as many as 16 overall conducting sections can be included within a lead body that has an OD of 0.031 inches. Such sizes and number of conductors were not achievable with prior known assembly techniques and lead configurations. Facilitating such a large number of conducting sections in such small OD lead bodies allows lead bodies to be used in applications where 8, 16, 32 or even more independent conductors are needed in very small diameter package.

Figure 14:
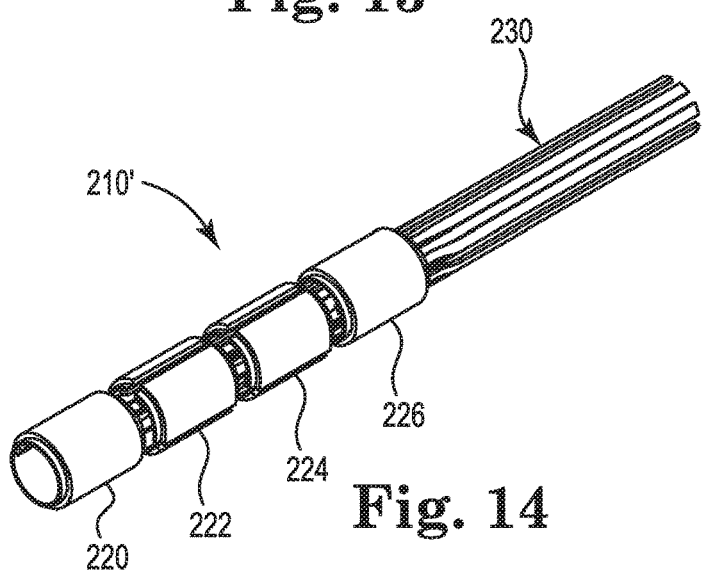
FIG. 14 illustrates a perspective view of an electrode assembly for a lead body in accordance with one embodiment.

As previously discussed, various combinations of segmented electrodes and ring electrodes are possible in accordance with various embodiments of a lead body. FIG. 14 illustrates electrode assembly 210' for a lead in accordance with one embodiment. Similar to prior discussed embodiments, electrode assembly 210' includes a plurality of conducting sections 230 that come from a sectioned hypotube (such as sectioned hypotube 40 or 140 above) and a plurality of electrodes 220, 222, 224, 226. In the illustration, electrodes 220, 222, 224, 226 appear after a centerless grinding process and electrodes 220 and 226 remain ring electrodes, that is, the electrodes extend 360° radially about the lead, while electrodes 222 and 224 include three electrode segments, each extending 120° radially about the lead.

Figure 15A:
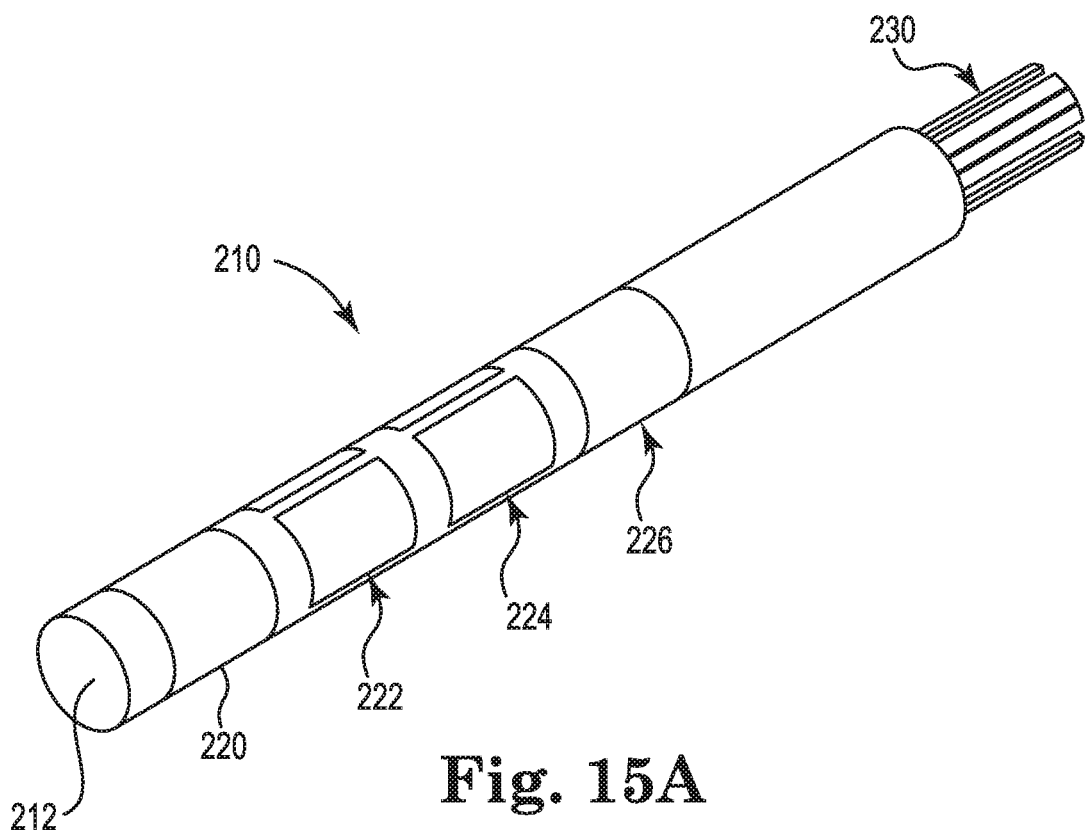
FIG. 15A illustrates a perspective view of a lead body with segmented and ring electrodes in accordance with one embodiment.

After molding material is flowed over electrode assembly 210', such as previously described in reference to FIG. 6, a lead body 210 with segmented and ring electrodes is formed in accordance with one embodiment. This is illustrated in FIG. 15A. This arrangement is sometimes referred to as a 1-3-3-1 electrode arrangement.

Figure 15B:
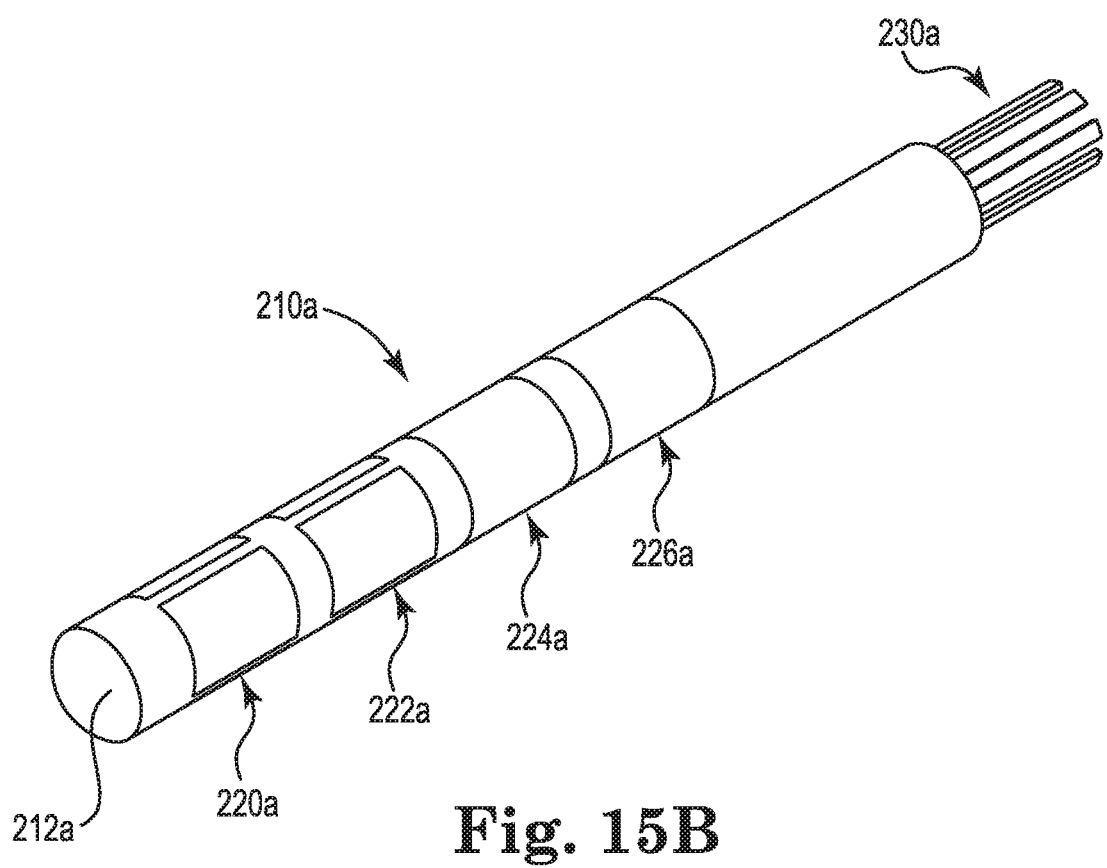
FIG. 15B illustrates a perspective view of a lead body with segmented and ring electrodes in accordance with one embodiment.

A similar process can be used to form lead body 210a with segmented and ring electrodes in a different configuration. As illustrated in FIG. 15B, lead body 210a, includes a plurality of conducting sections 230a that come from a sectioned hypotube (such as sectioned hypotube 40 or 140 above) and a plurality of electrodes 220a, 222a, 224a, 226a. In the illustration, electrodes 220a, 222a, 224a, 226a are the result of a centerless grinding process and electrodes 224a and 226a remain ring electrodes, that is, the electrodes extend 360° radially about the lead, while electrodes 220a and 222a include three electrode segments, each extending 120° radially about the lead. This arrangement is sometimes referred to as a 3-3-1-1 electrode arrangement.

Other similar arrangements are readily possible, such as 2×2 (two electrodes, each with two segments), 3×3 (three electrodes, each with three segments), 4×2 (four electrodes, each with two segments), 2×3 (two electrodes, each with three segments), 3×3 (three electrodes, each with three segments), 4×3 (four electrodes, each with three segments), 2×4 (two electrodes, each with four segments), 3×4 (three electrodes, each with four segments), 4×4 (four electrodes, each with four segments), etc. There are practical limits to the number of electrodes and corresponding segments that can be made given the size constraints for the lead body. In one case, the limits are given by: $2<x<4$, $2<y<6$, where x is the number of electrodes and y is the number of segments for each electrode, where there are 16 conducting sections in the sectioned hypotube.

Other configurations are readily possible, including clocked or linear electrodes, or electrodes assembled in a spiral pattern. The design of the sectioned hypotube is simply adjusted to match the desired electrode pattern. Straightening the cut lines of the sectioned hypotube facilitate a rotated or spiral pattern to the electrodes in the final assembly.

Figure 16:
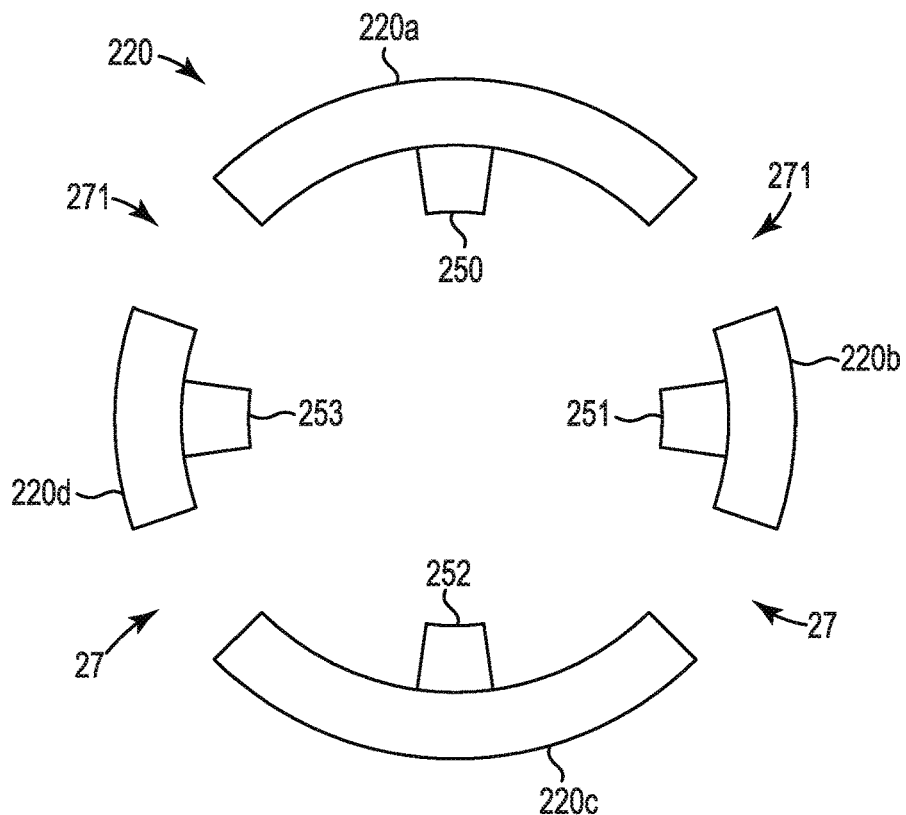
FIG. 16 illustrates a partial end view, with portions removed, of a lead body with in accordance with one embodiment.

In addition to providing differing numbers of electrodes, electrode segments and combinations thereof, the actual size of the electrode segments within a particular electrode can also be varied. FIG. 16 illustrates a partial end sectional view of an electrode 220 with electrode segments 220a, 220b, 220c and 220d. Each electrode segment is respectively coupled to one conducting section 250, 251, 252 and 253. Each electrode segment 220a, 220b, 220c and 220d is separated by openings 271. As illustrated, electrode segments 220a and 220c are longer segments than are electrode segments 220b and 220d. In one embodiments, electrode segments 220a and 220c extend nearly 90 degrees about the outer circumference of the lead body, while electrode segments 220a and 220c extend less than 45 degrees about the outer circumference of the lead body. Other configurations are possible, for example, where each electrode segment has a different segment length.

Figure 17:
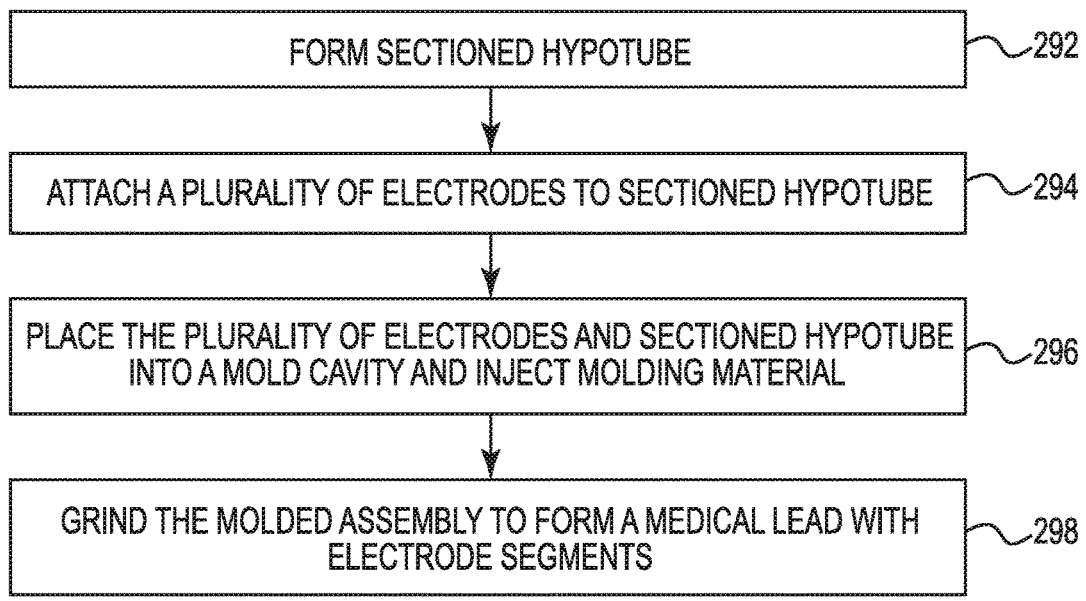
FIG. 17 illustrates a method of forming a lead body with segmented electrodes in accordance with one embodiment.

FIG. 17 illustrates a method of forming a segmented electrode lead body, such as leads 10 and 210, in accordance with one embodiment. First, at step 292, a sectioned hypotube, such as previously described sectioned hypotube 40 and hypotube 140, is formed. In one embodiment, sections are cut into a solid hypotube to form the sectioned hypotube. The sectioned hypotube may be formed by any of a variety of processing techniques, including laser cutting, or metal etching or the like. The sectioned hypotube has a plurality of conducting sections such that each extend from a proximal to a distal end and such that each are electrically isolated from the other.

At step 294, a plurality of electrodes are attached to each of the plurality of conducting sections of the sectioned hypotube to form an electrode assembly. In one embodiment, a plurality of non-ground electrodes are placed adjacent the distal end of the sectioned hypotube. In one embodiment, each of the plurality of conducting sections are welded to a discrete location on each of the plurality of non-ground electrodes, such that one conducting section will correspond with one electrode segment after the non-ground electrode is segmented.

At step 296, the electrode assembly including the plurality of electrodes attached to the plurality of conducting sections of the sectioned hypotube is placed in a mold cavity and molding material is formed over the electrode assembly. The mold material fills all spaces within the electrode assembly, including filling around the combination of non-ground electrodes and the plurality of conducting sections.

At step 298, the molded electrode assembly is ground inward from its outer periphery using a centerless grinding process to form a lead body with segmented electrodes.

The various described steps are not necessarily required in a particular order. For example, a centerless grinding process may be applied to the electrode assembly before the combination is placed into a mold cavity. The injection molding process can then be the last step in producing the finished lead.

In order to fully operate a segmented electrode lead body, such as leads 10 and 210, the proximal end of such a lead body is generally provided with a number of ring contacts that match up with the combination of electrode rings and electrode segments, such that each ring contact corresponds to one segment of an electrode or to one ring of an electrode ring.

Figure 18:
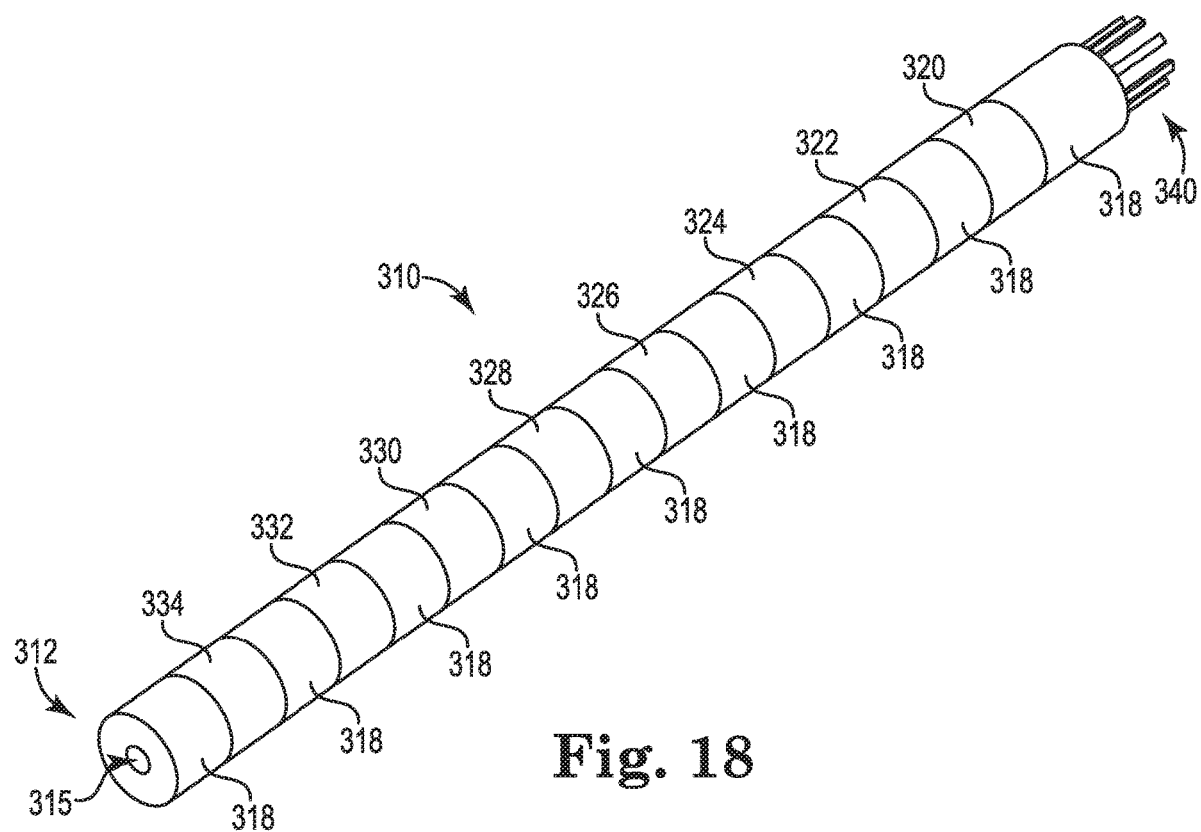
FIG. 18 illustrates a perspective view of a lead body with proximal connectors in accordance with one embodiment.

FIG. 18 illustrates a perspective view of a lead body 310 in accordance with one embodiment. In one embodiment, lead 310 includes, adjacent its proximal end 312, eight ring contacts 320, 322, 324, 326, 328, 330, 332, 334. In other embodiments, more or fewer ring contacts may be included. In one embodiment, ring contacts 320, 322, 324, 326, 328, 330, 332, 334 are provided on the proximal end 312 of lead 310 for plugging in to a medical device. Each ring contact 320, 322, 324, 326, 328, 330, 332, 334 is electrically isolated from each other by insulative material 318.

In one embodiment, lead body 310 is coupled with a distal end, such as lead bodies 10 and 210 described above, which distal end is then placed adjacent tissue that is to be sensed or stimulated. Then, a medical device either transmits or receives energy via ring contacts 320, 322, 324, 326, 328, 330, 332, 334, which are all electrically conductive and which are independently coupled to the medical device. Each of ring contacts 320, 322, 324, 326, 328, 330, 332, 334 can couple independently to a location to be sensed or stimulated via one conducting section of a plurality of conducting sections 340, as will be explained in more detail below. In one embodiment, lead body 310 also includes a center lumen 315, which can be used to provide access from the proximal end to the distal end of lead body 310.

Lead body 310 in accordance with embodiments described herein, allow for the manufacture of leads having increased number of ring contacts, yet at the same time maintaining a very small overall diameter. Increased number of ring contacts is useful in a variety of applications. For example, lead 310 can be used in deep brain stimulation (DBS), in which lead 310 delivers electrical pulses into one or several specific sites within the brain of a patient to treat various neurological disorders, such as chronic pain, tremors, Parkinson's disease, dystonia, epilepsy, depression, obsessive-compulsive disorder, and other disorders. In other applications, lead 310 may be configured for spinal cord stimulation, peripheral nerve stimulation, dorsal root stimulation, cortical stimulation, ablation therapies, cardiac rhythm management leads, various catheter configurations for sensing, and various other therapies where directional sensing or stimulation are needed. In many such applications, a large number of ring contacts in a small diameter is very useful.

Figure 19:
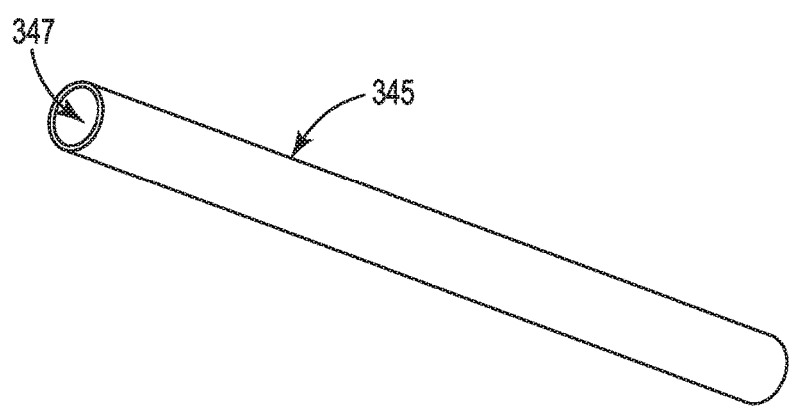
FIG. 19 illustrates a perspective view of hypotube for manufacturing a lead in accordance with one embodiment.

In one embodiment, the manufacture of lead 310 begins with a hypotube 345, such as illustrated in FIG. 19. Hypotube 345 is a tube that has an open center lumen 347 and also has a very small micro outside diameter, for example, as small as 0.040 or 0.005 inches. Hypotubes 345 can be any of a variety of materials, and in one embodiment is stainless steel. In one embodiment, hypotube 345 is sectioned into a plurality of conducting sections via any number of sectioning methods. In one embodiment, hypotube 345 is cut into sections using a laser. In another embodiment, it is chemically etched into sections. Other methods are also possible on accordance with other embodiments.

Figure 20A:
FIG. 20A illustrates a side view of a sectioned hypotube for a lead body in accordance with one embodiment.

Sectioned hypotube 350 illustrated in FIG. 20A is a hypotube, such as hypotube 345, that has been sectioned to form a plurality of conducting sections 340. In one embodiment, first and second unsectioned portions 352 and 354 of sectioned hypotube 350 remain solid tube portions, and are not sectioned. Between first and second unsectioned portions 352 and 354, a plurality of conducting sections 340 are formed by the removal of material from hypotube 345, for example, by laser cutting. The number of conducting sections within plurality of conducting sections 340 can be varied such that one conducting section is provided for each ring contact. The conducting sections are all formed in the cylindrical diameter of the hypotube 345, such that the inner lumen 347 of sectioned hypotube 340 extends within the plurality of conducting sections 340, and such that the outer profile of each conducting section retains the cylindrical diameter of hypotube 340.

Figure 20B:
FIG. 20B illustrates a top view of a flattened sectioned hypotube illustrated in FIG. 20A.

In one embodiment, the plurality of conducting sections 340 includes 8 individual conducting sections 360-367. Because the conducting sections 360-367 are arranged radially about the circumference of sectioned hypotube 350, only a portion are visible in the side view of sectioned hypotube 350 in FIG. 20A. Accordingly, FIG. 20B illustrates sectioned hypotube 350 illustrated in FIG. 20A, but in a flattened state. In actual use, sectioned hypotube 350 is not flattened and remains in a cylindrical or tube shape, but is illustrated in FIG. 20B as flattened simply so that all 8 conducting sections 360-367 of the plurality of conducting sections 340 are visible in a two-dimensional drawing.

Figure 21:
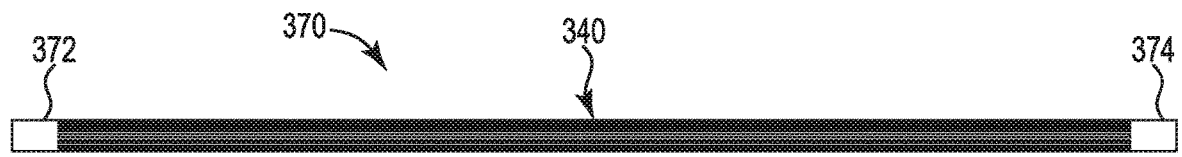
FIG. 21 illustrates a side view of a sectioned hypotube for a lead body in accordance with one embodiment.

As mentioned, a sectioned hypotube can have any of a variety of numbers of conducting sections. For example, FIG. 21 illustrates sectioned hypotube 370 in accordance with one embodiment, which has 16 conducting sections in its plurality of conducting sections 340. Similar to the previous embodiment, sectioned hypotube 370 includes first and second unsectioned portions 372 and 374, which remain solid tube portions on either side of the plurality of conducting sections 340.

Figure 22A:
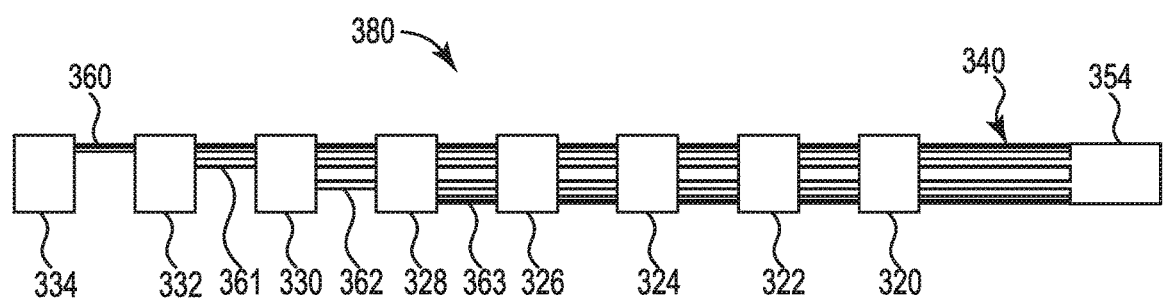
FIG. 22A illustrates a side view of a ring contact assembly including a sectioned hypotube for a lead body in accordance with one embodiment.
Figure 22B:
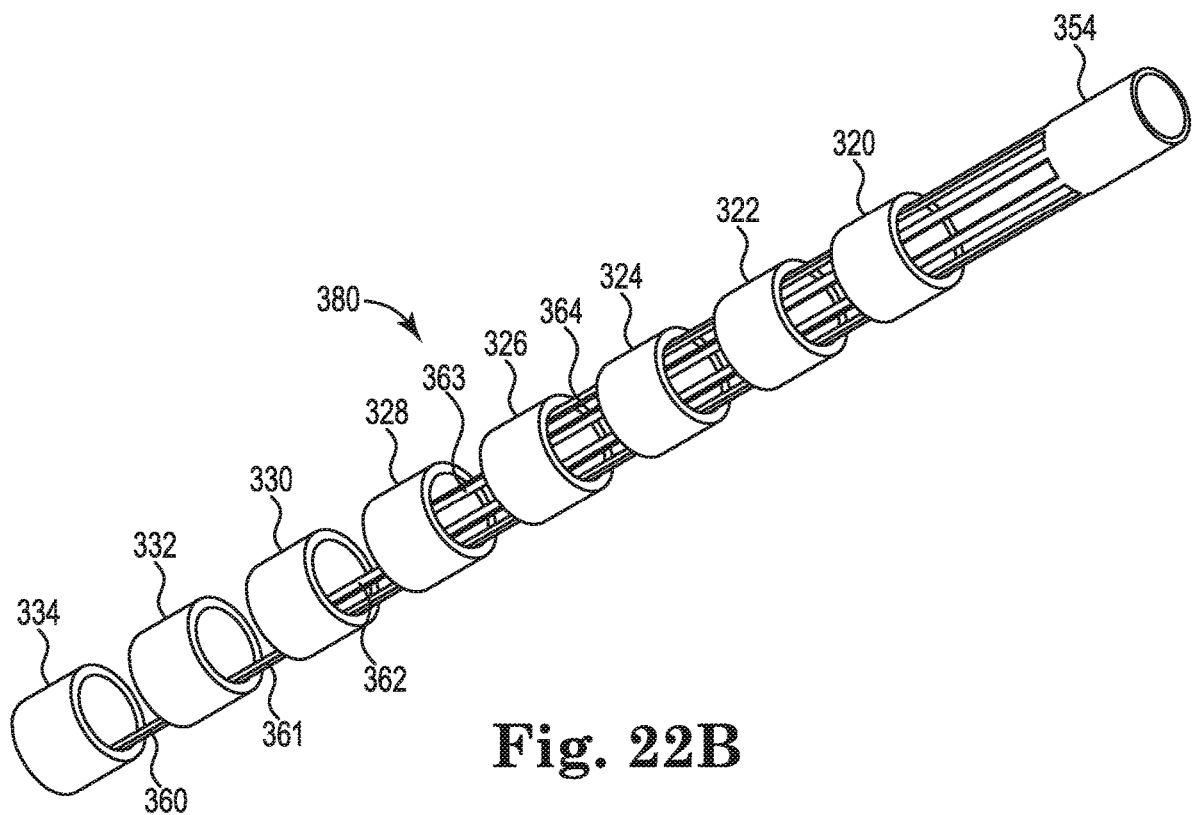
FIG. 22B illustrates a perspective view of the ring contact assembly from FIG. 22A in accordance with one embodiment.

FIGS. 22A and 22B illustrates ring contact assembly 380 for a lead body in accordance with one embodiment. In one embodiment, ring contacts 320, 322, 324, 326, 328, 330, 332, 334 are placed over sectioned hypotube 350 to form ring contact assembly 380. In one embodiment, each of ring contacts 320, 322, 324, 326, 328, 330, 332, 334 is placed over sectioned hypotube 350 and individually coupled to just one of the plurality of conducting sections 340. In one embodiment, conducting section 360 is coupled to ring contact 334, conducting section 361 is coupled to ring contact 332, conducting section 362 is coupled to ring contact 330, conducting section 363 is coupled to ring contact 328, conducting section 364 is coupled to ring contact 326, conducting section 365 is coupled to ring contact 324, conducting section 366 is coupled to ring contact 322, and conducting section 367 is coupled to ring contact 320. Not all couplings are visible in the figures because of the cylindrical nature of the assembly, but the connections on the "backside" of the assembly, as viewed in the figure, are similar to those that are visible.

In one embodiment, as the proximal end of each conducting section is coupled to one ring electrode, the remaining proximal portion of the conducting section is clipped off. Accordingly, once each conducting section is coupled to a ring contact, the first unsectioned portion 352 of sectioned hypotube 350 is removed. In one embodiment, second unsectioned portion 354 of sectioned hypotube 350 is left in place for further processing, as will be discussed below. In one embodiment, each conducting section is coupled to one ring electrode by laser welding. In one embodiment, each conducting section is coupled to one ring electrode with an adhesive. In other embodiments, conducting sections can be coupled to ring electrode by other means.

In one embodiment, sectioned hypotube 350 is covered with an insulative material. As such, when each conducting section is welded to an individual ring contact, the insulative material will be ablated in the area of the weld such that the particular conducting section is electrically coupled only to the individual ring contact to which it is welded, but remains electrically insulated from all the other ring contacts via the insulative material. In this way, ring contact assembly 380 has one conducting section electrically coupled to one, and only one, ring contact.

Figure 23A:
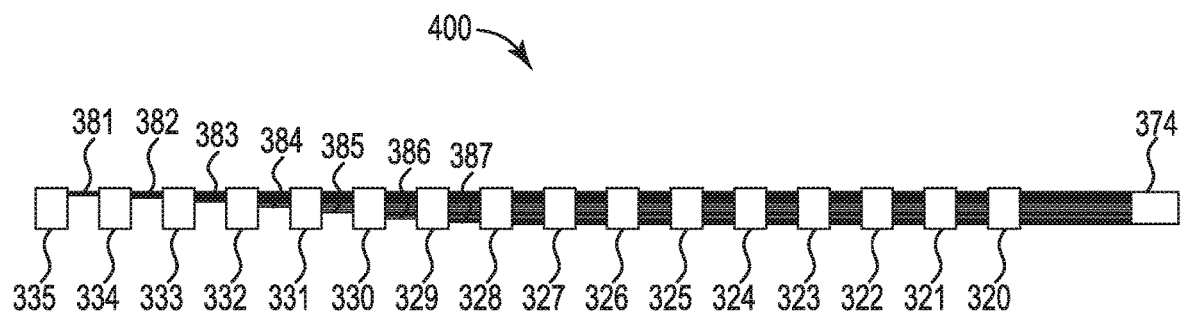
FIG. 23A illustrates a side view of a ring contact assembly including a sectioned hypotube for a lead body in accordance with one embodiment.
Figure 23B:
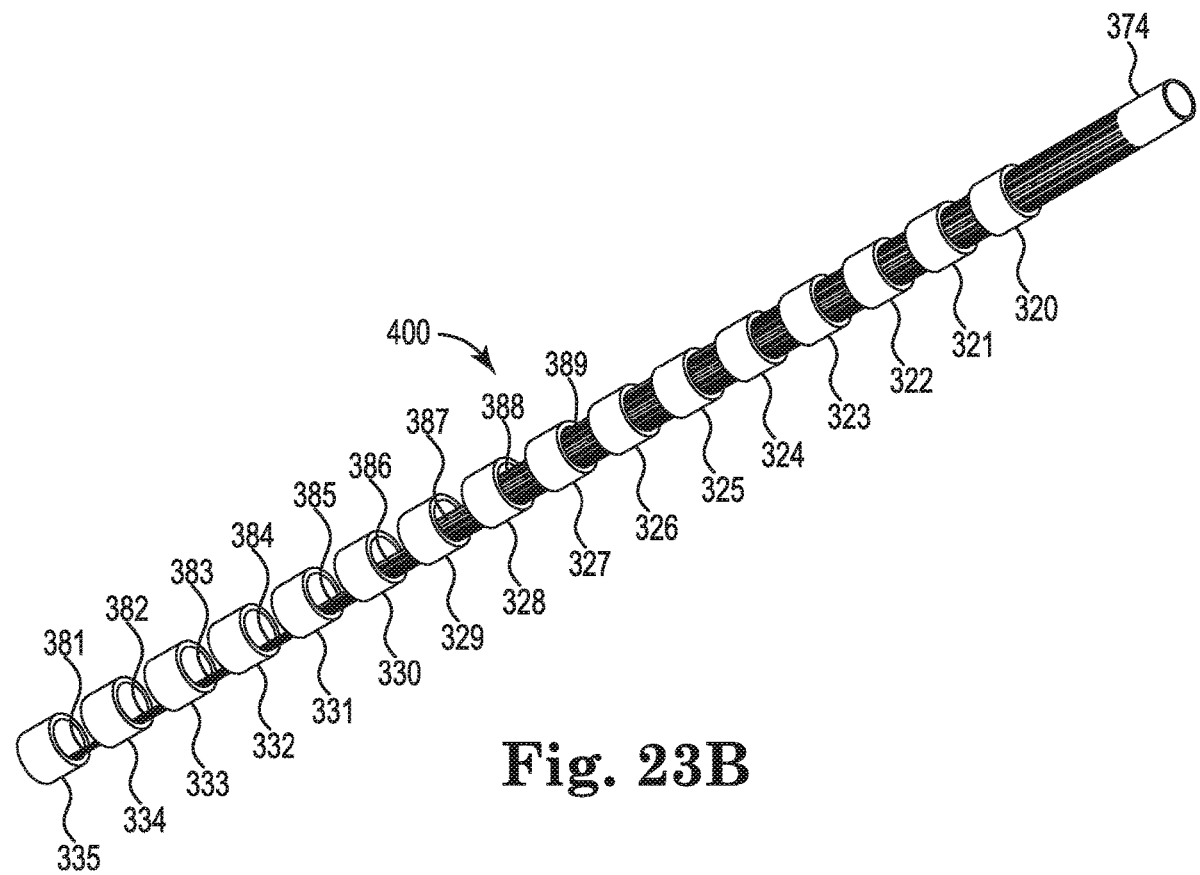
FIG. 23B illustrates a perspective view of the ring contact assembly of FIG. 23A in accordance with one embodiment.

As mentioned, a sectioned hypotube can have any of a variety of numbers of conducting sections. For example, FIGS. 23A and 23B illustrates ring contact assembly 400 having 16 ring contacts and corresponding conducting sections for a lead in accordance with one embodiment. In one embodiment, ring contacts 320, 321, 322, 323, 324, 325, 326, 327, 328, 329, 330, 331, 332, 333, 334, 335 are placed over sectioned hypotube 370 to form ring contact assembly 400. In one embodiment, each of ring contacts 320, 321, 322, 323, 324, 325, 326, 327, 328, 329, 330, 331, 332, 333, 334, 335 is placed over sectioned hypotube 370 and individually coupled to just one of the plurality of conducting sections 340. In one embodiment, conducting section 381 is coupled to ring contact 335, conducting section 382 is coupled to ring contact 334, conducting section 383 is coupled to ring contact 333, conducting section 384 is coupled to ring contact 332, conducting section 385 is coupled to ring contact 331, conducting section 386 is coupled to ring contact 330, conducting section 387 is coupled to ring contact 329, and conducting section 388 is coupled to ring contact 328, conducting section 389 is coupled to ring contact 327, conducting section 390 is coupled to ring contact 326, conducting section 391 is coupled to ring contact 325, conducting section 392 is coupled to ring contact 324, conducting section 393 is coupled to ring contact 323, conducting section 394 is coupled to ring contact 322, conducting section 395 is coupled to ring contact 321, and conducting section 396 is coupled to ring contact 320. Again, not all couplings are visible in the figures because of the cylindrical nature of the assembly, but the connections on the "backside" of the assembly, as viewed in the figure, are similar to those that are visible. In this way, similar to ring contact assembly 380, ring contact assembly 400 has one conducting section electrically coupled to one, and only one, ring contact.

Figure 24:
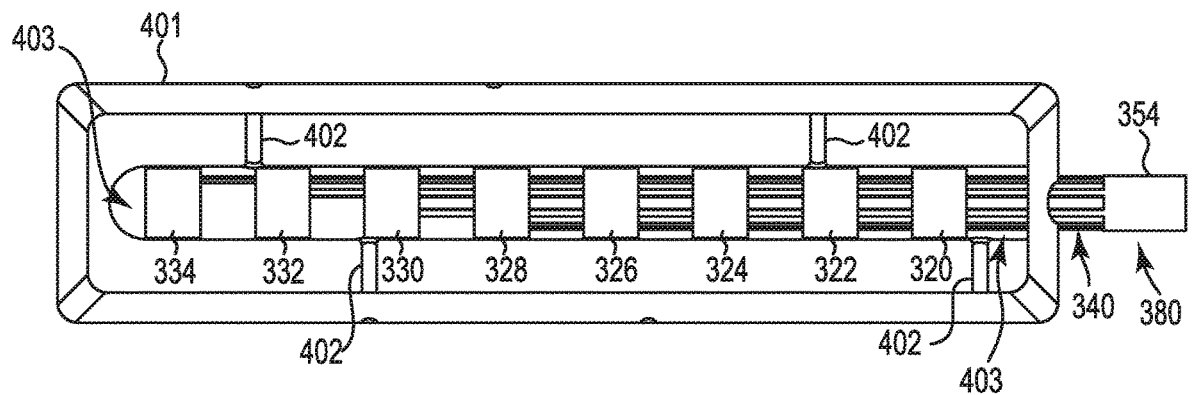
FIG. 24 illustrates a top view of a ring contact assembly including a sectioned hypotube for a lead body in a mold cavity in accordance with one embodiment.

FIG. 24 illustrates ring contact assembly 380 for lead 310 placed within an injection mold 401 in accordance with one embodiment. Injection mold 401 includes mold cavity 403, in which ring contact assembly 380 is placed, and mold gates 402. Once mold cavity 403 is closed against its mirror image cavity (not illustrated), an insulative molding material, such as thermoplastic or elastomer insulation, is flowed into cavity 403 via mold gates 402. The insulative molding material fills all spaces within ring contact assembly 380, including filing around the combination of ring contacts 320, 322, 324, 326, 328, 330, 332, 334 and plurality of conducting sections 360-367. In one embodiment, a mandrel or core pin is inserted into the center lumen of ring contact assembly 380 before placing it into mold 403 in order to prevent mold material from flowing into the assembly center and maintaining its central lumen.

In one embodiment, first unsectioned portion 352 of sectioned hypotube 350 is cut off as each of conducting sections 360-367 are welded to the respective ring contacts 320-334. Second unsectioned portion 354, however, can be left attached while ring contact assembly 380 is overmolded, so that the plurality of conducting sections 340 are physically supported at one end by the weld to each respective ring contact, and physically supported at the other end by second unsectioned portion 354, such that they are not significantly disturbed or moved out of alignment by the force with which the molding material enters cavity 403.

Figure 25A:
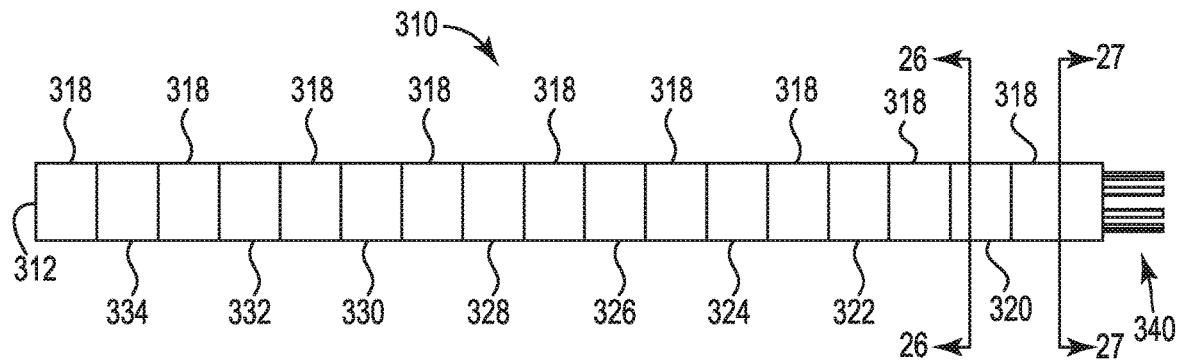
FIG. 25A illustrates a side view of a ring contact assembly including a sectioned hypotube after molding in accordance with one embodiment.
Figure 25B:
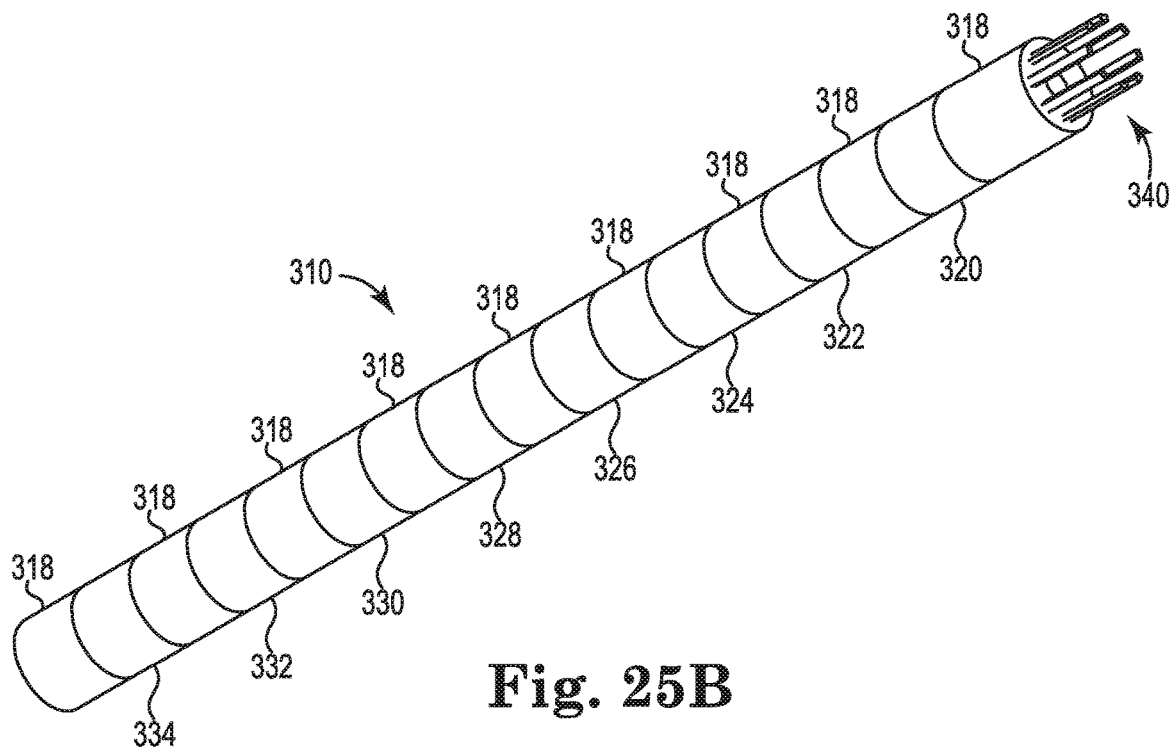
FIG. 25B illustrates a perspective view of the ring contact assembly of FIG. 25A in accordance with one embodiment.

FIGS. 25A-25B illustrate a side and perspective views of the ring contact assembly 380 after the insulative material 318 solidifies, thereby forming lead body 310. Insulative material 318 fills the voids between each of ring contacts 320-334, such that each is electrically isolated from each other by the insulative material 318. The insulative material 318 also flows over and between each of conducting sections 360-367, such that they are surrounded and firmly secured with the molding material, and electrically isolated from each other.

In one embodiment, the outer diameter of each of ring contacts 320-334 match the inner diameter of mold cavity 403, such that the solidified insulative material 318 has the same outer diameter as ring contacts 320-334, thereby forming lead body 310 with a uniform and smooth outer diameter. In one embodiment, once ring contact assembly 380 is removed from the mold cavity 403, it is subjected to a centerless grinding process to form lead body 310 with a uniform smooth outer diameter.

FIGS. 25A-25B illustrate the plurality of conducting sections 340 extending from lead 310 opposite the proximal end. In one embodiment, the plurality of conducting sections 340 include 8 conducting sections, one each attached to one corresponding ring contact 320-334. The plurality of conducting sections 340 can then be attached to other sections of the lead body, for example, sections that may sense or provide signals or pulses to an area of tissue, such as lead bodies 10 and 210 discussed above.

Figure 26:
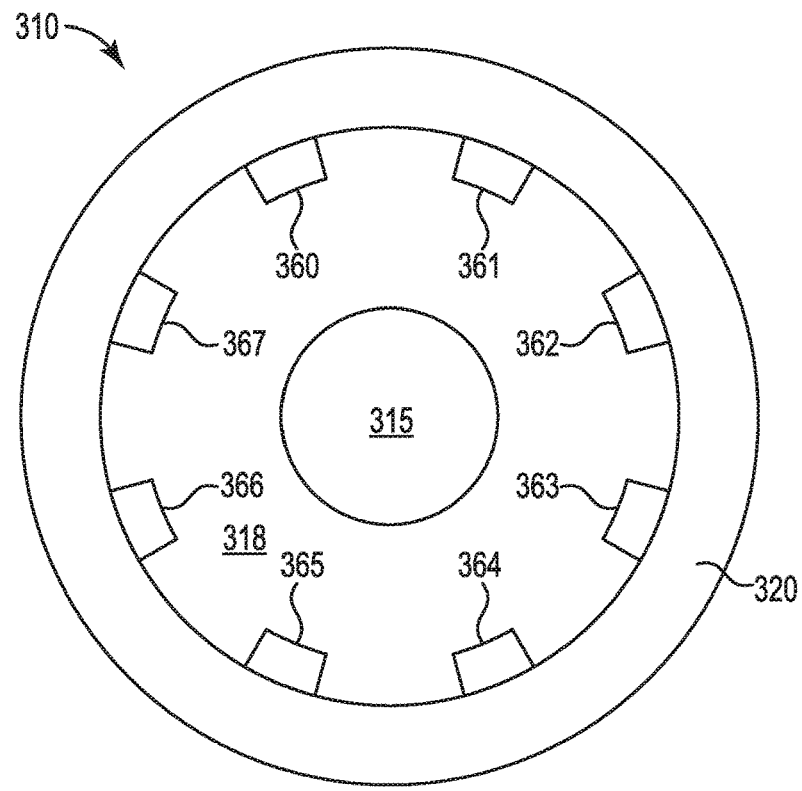
FIG. 26 illustrates a sectional view of the ring contact assembly of FIG. 25A, taken at line 26-26, in accordance with one embodiment.

FIG. 26 illustrates a sectional view of lead 310 taken through ring contact 320 along line 26-26 in FIG. 25A in accordance with one embodiment. As illustrated, conducting sections 360-367 pass through the inner diameter of ring contact 320, and all but conducting section 367, continue on past ring contact 320 in order to be coupled with another ring contact toward the proximal end 312. Conducting section 367 is coupled to ring contact 320, such that they are both physically and electrically coupled thereto. The remaining conducting sections merely pass through ring contact 320, such that they are neither physically nor electrically coupled thereto. In one embodiment, solidified insulative material 318 supports all the conducting sections, and also defines center lumen 315 (maintained during the injection molding by the mandrel or core pin) of lead body 310.

Figure 27:
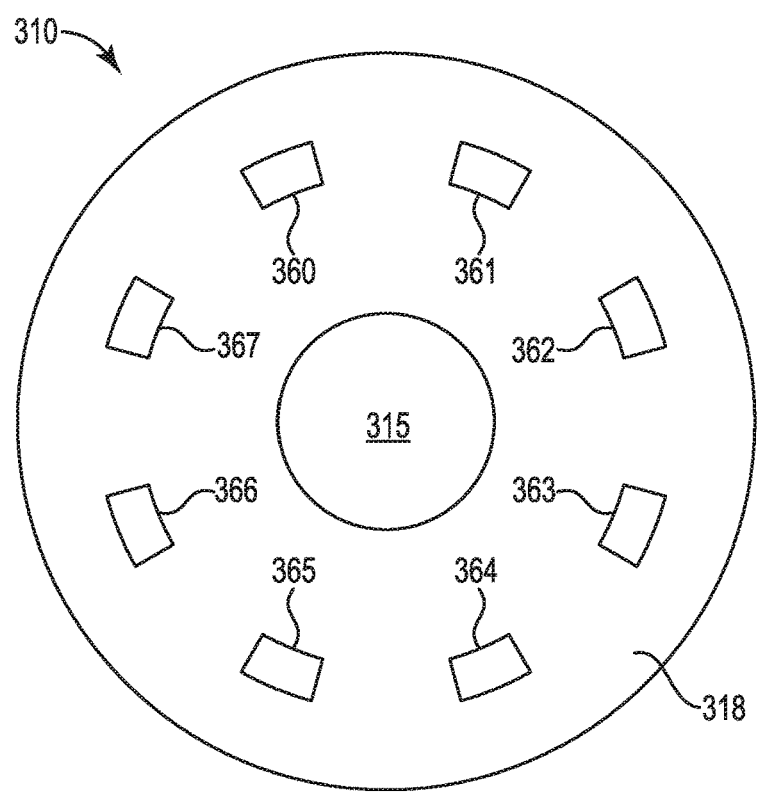
FIG. 27 illustrates a sectional view of the ring contact assembly of FIG. 25A, taken at line 27-27, in accordance with one embodiment.

FIG. 27 illustrates a sectional view of lead 310 taken between ring contact 320 and ring contact 322 along line 27-27 in FIG. 25A in accordance with one embodiment. As illustrated, conducting sections 360-367 pass through, and are supported and insulated by insulation material 318, which also defines center lumen 315.

As illustrated in FIGS. 25A-25B, ring contacts 320-334 can be uniformly spaced apart along the axis of lead 310 near the proximal end 312, such that each ring 320-334 aligns with an electrical contact within a generator or implantable medical device slot. As such, each ring contact 320-334 can be individually accessed for sending and receiving electrically signals to and from the implantable medical device. The spacing between each of the ring contacts 320-334 can readily be tailored to the requirements within the particular implantable medical device slot into which lead 310 will be inserted, so that they align with the corresponding contacts within the medical device slot.

Figure 28A:
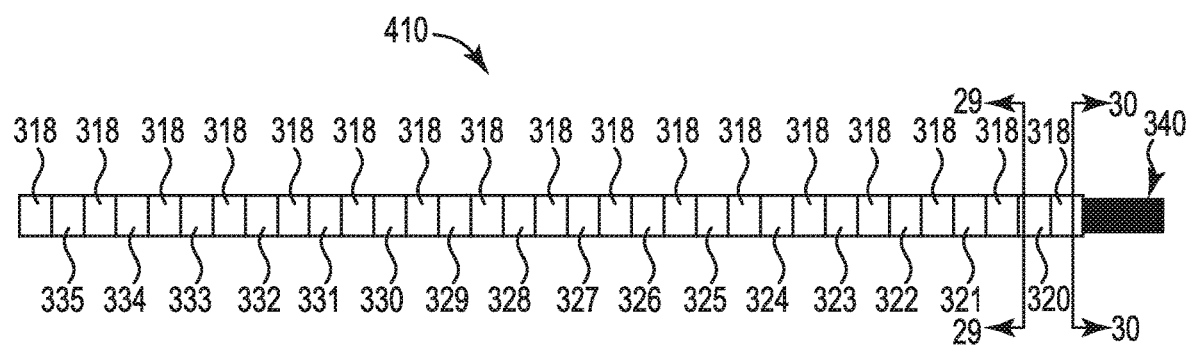
FIG. 28A illustrates a side view of a ring contact assembly including a sectioned hypotube after molding in accordance with one embodiment.
Figure 28B:
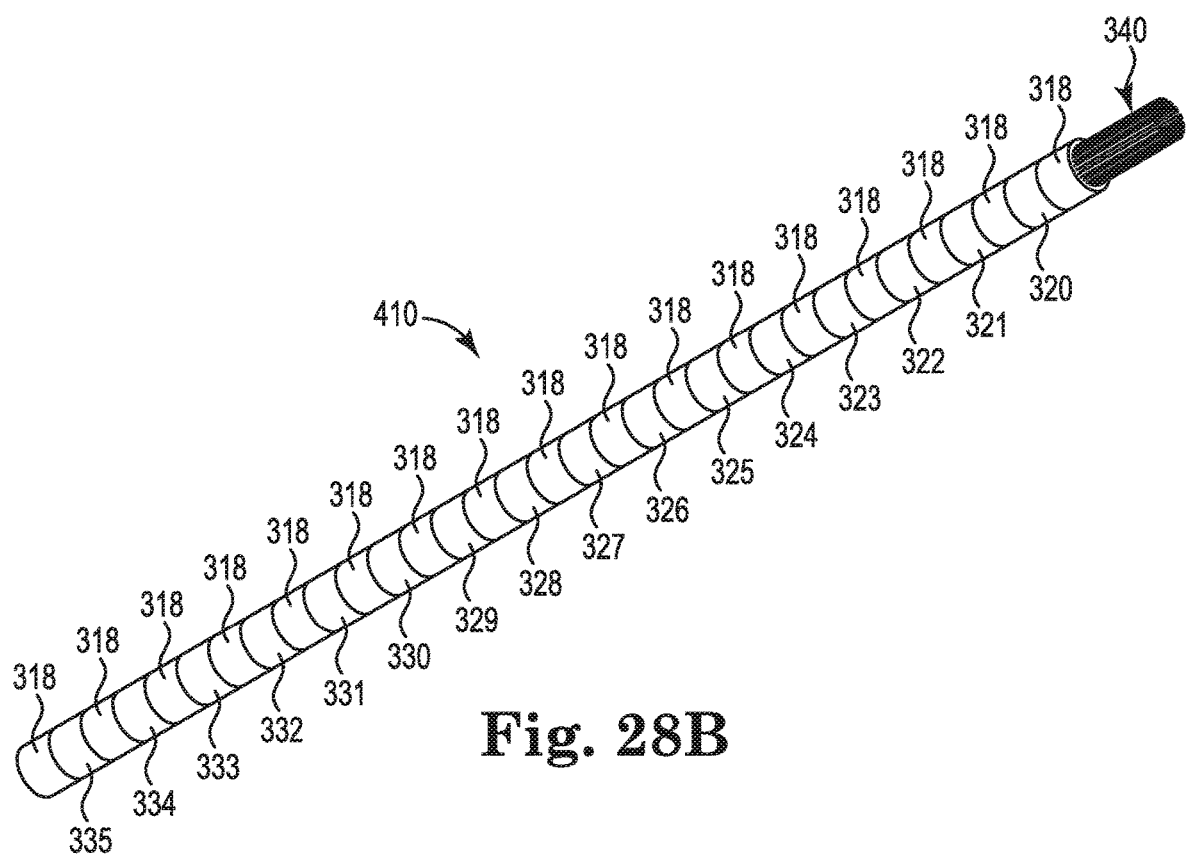
FIG. 28B illustrates a perspective view of the ring contact assembly of FIG. 28A in accordance with one embodiment.

Furthermore, the number of ring contacts can also be adjusted according to certain embodiments. For example, FIGS. 25A-25B illustrate a lead body 310 having 8 ring contacts spaced along the proximal end 312. FIGS. 28A-28B illustrate a side and perspective views of the lead body 410 having 16 ring contacts 320-335 spaced along its proximal end. Lead body 410 can be formed similarly to that described above for lead body 310.

For example, ring contact assembly 400 illustrated in FIGS. 23A and 23B can be placed in a mold cavity, such as illustrated in FIG. 24. After a similar molding process as previously described, the insulative material 318 solidifies, thereby forming lead body 410 illustrated in FIGS. 28A-28B. Just as for lead 310, insulative material 318 fills the voids between each of ring contacts 320-335 in lead 410, such that each is electrically isolated from each other by the insulative material 318. The insulative material 318 also flows over and between each of conducting sections 381-396, such that they are surrounded and firmly secured with the molding material, and electrically isolated from each other.

Figure 29:
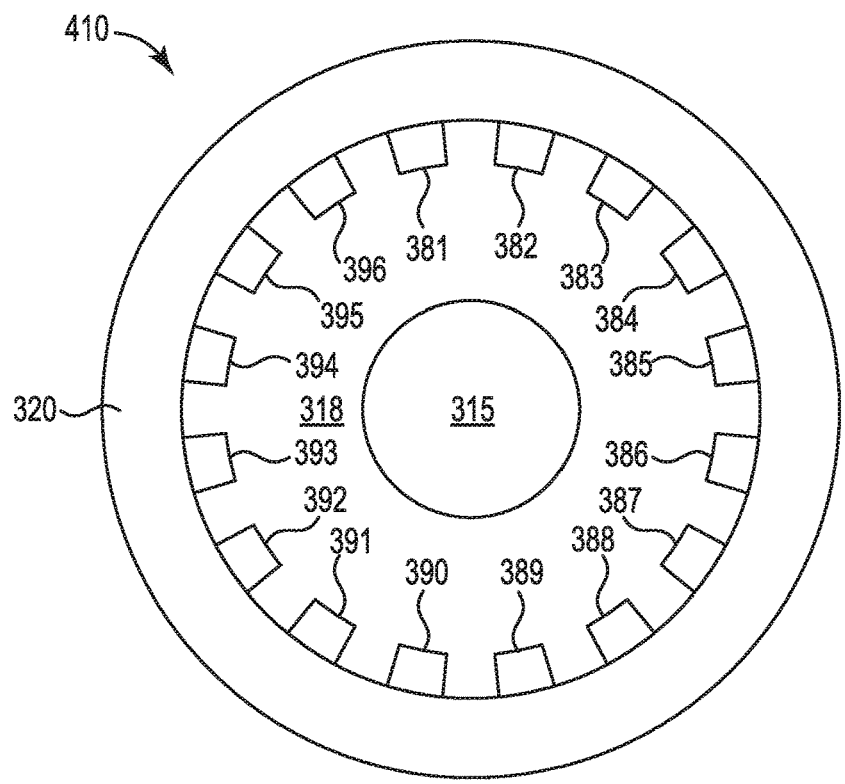
FIG. 29 illustrates a sectional view of the ring contact assembly of FIG. 28A, taken at line 29-29, in accordance with one embodiment.

FIG. 29 illustrates a sectional view of lead 410 taken through ring contact 320 along line 29-29 in FIG. 28A in accordance with one embodiment. As illustrated, conducting sections 381-396 pass through the inner diameter of ring contact 320, and all but conducting section 381, continue on past ring contact 320 in order to be coupled with another ring contact toward the proximal end. Conducting section 381 is coupled to ring contact 320, such that they are both physically and electrically coupled thereto. The remaining conducting sections merely pass through ring contact 320, such that they are neither physically nor electrically coupled thereto. In one embodiment, solidified insulative material 318 supports all the conducting sections, and also defines center lumen 315.

Figure 30:
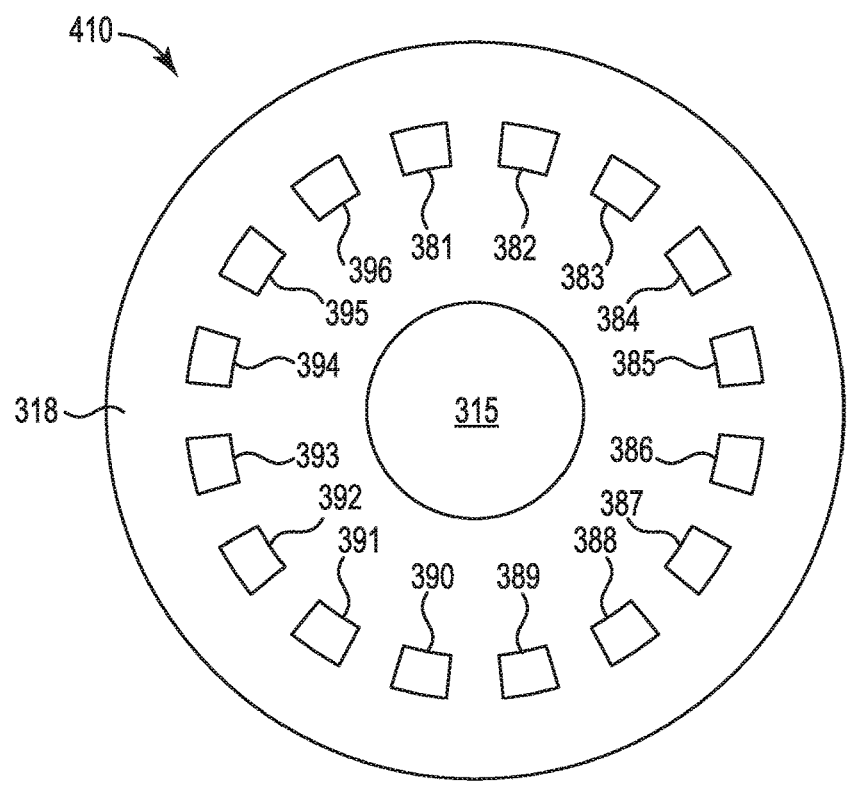
FIG. 30 illustrates a sectional view of the ring contact assembly of FIG. 28A, taken at line 30-30, in accordance with one embodiment.

FIG. 30 illustrates a sectional view of lead 410 taken between ring contact 320 and ring contact 321 along line 30-30 in FIG. 28A in accordance with one embodiment. As illustrated, conducting sections 381-396 pass through, and are supported and insulated by insulation material 318, which also defines center lumen 315.

The plurality of conducting sections 340 extending from lead 410 include 16 conducting sections 381-396, one each attached to one corresponding ring contact 320-335. The plurality of conducting sections 340 can then be attached to other sections of the lead body, for example, sections that may sense or provide signals or pulses to an area of tissue, such as lead bodies 10 and 210 discussed above.

Figure 31:
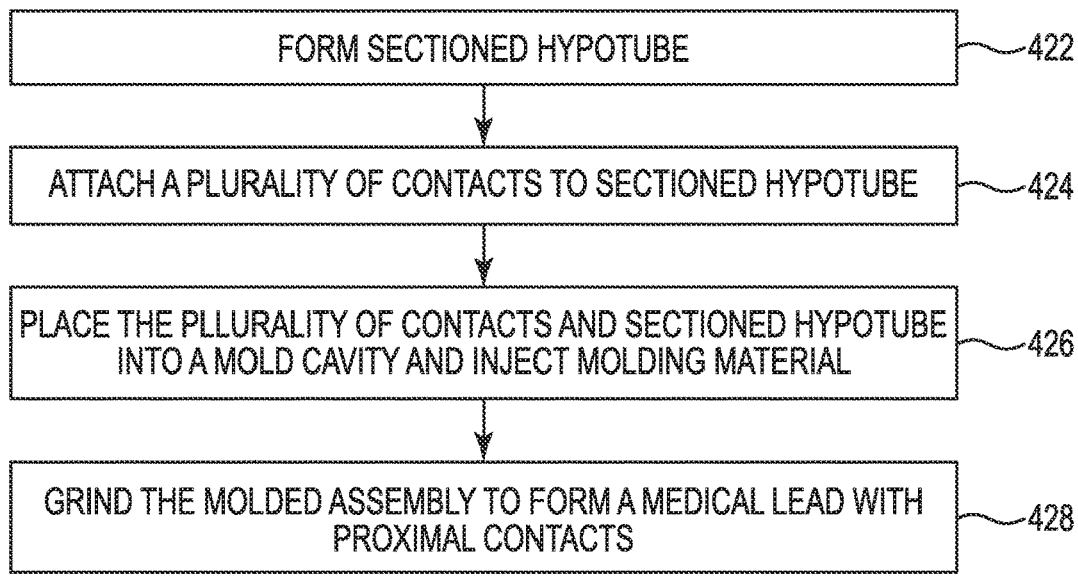
FIG. 31 illustrates a method of forming a lead body with proximal connectors in accordance with one embodiment.

FIG. 31 illustrates a method of forming a lead body, such as leads 310 and 410, in accordance with one embodiment. First, at step 422, a sectioned hypotube, such as previously described sectioned hypotube 350 and hypotube 370, is formed. In one embodiment, sections are cut into a solid hypotube to form the sectioned hypotube. The sectioned hypotube may be formed by any of a variety of processing techniques, including laser cutting, or metal etching or the like. The sectioned hypotube has a plurality of conducting sections such that each extend from a proximal to a distal end and such that each are electrically isolated from the other.

At step 424, a plurality ring contacts are attached to each of the plurality of conducting sections of the sectioned hypotube to form a ring contact assembly. In one embodiment, a plurality of ring contact are placed adjacent the proximal end of the sectioned hypotube. In one embodiment, each of the plurality of conducting sections are welded to a discrete location on each of the plurality ring contacts, such that one conducting section will correspond with one ring contact.

At step 426, the ring contact assembly, including the plurality of ring contacts attached to the plurality of conducting sections of the sectioned hypotube, is placed in a mold cavity and molding material is formed over the ring contact assembly. The mold material fills all spaces within the ring contact assembly, including filling around the combination of ring contacts and the plurality of conducting sections.

At step 428, the molded ring contact assembly is ground inward from its outer periphery using a centerless grinding process to form a lead body with ring contacts. The various described steps are not necessarily required in a particular order.

Using sectioned hypotubes, such as described herein, lead bodies with very small dimensions, yet with increased numbers of ring contacts, are achievable. For example, lead bodies 310 and 410, using sectioned hypotubes 350 and 370, allows conductors having small sizes that were prohibitively small with prior configurations of lead bodies. Because sectioned hypotubes can be better controlled, lead bodies having conducting sections with very small size diameter wires are achievable. For example, in various embodiments, a conducting section having an outer diameter (OD) as small as 0.001 inches can be coupled to a ring contact within a lead body.

Accordingly, because such a tiny conducting section can be effectively joined to a ring contact and fully secured a lead body, the number of conductors that can be included within a lead body can be increased over previous configurations, and its overall outer diameter can be quite small as well. In the embodiments illustrated in figures, as many as 16 conducting sections were included within lead body 410. Also because of the small OD of the conducting sections, a relatively small OD for the lead body is also achievable despite the large number of conductors.

In one embodiment, the number of conducting sections that can be included within a lead body is a function of the OD of each of the conducting sections. In various embodiments, the following Table 2 illustrates achievable conducting section OD with associated achievable lead body overall OD and overall number of conducting sections:

TABLE 2

| | Achievable Lead Diameter | |
| --- | --- | --- |
| | 8 Channel | 16 Channel |
| Conducting Section OD (in) .001" | .021" | .031" |
| .003" | .031" | .051" |
| .005" | .041" | .064" |
| .010" | .064" | .103" |

As illustrated, when coupling a conducting section that has an OD of 0.001 inches to a ring conductor in a lead body, as many as 8 overall conducting sections can be included within a lead body that has an OD of 0.021 inches, and as many as 16 overall conducting sections can be included within a lead body that has an OD of 0.031 inches. Such sizes and number of conductors were not achievable with prior known assembly techniques and lead configurations. Facilitating such a large number of conducting sections in such small OD lead bodies allows lead bodies to be used in applications where 8, 16, 32 or even more independent conductors are needed in very small diameter package.

Where lead bodies, such as 10, 210, 310 and 410 discussed above, are made using sectioned hypotubes, such as 40, 140, 350 and 372 discussed above, coupling conducting sections from the hypotube to respective electrode segments and ring contacts have superior connections compared to prior designs. Because sectioned hypotubes are formed beginning with hypotubes that are then sectioned, the outer profile of the conducting sections are arced, because they substantially retain the outer periphery of the original hypotube. As such, the outer periphery of the conducting sections will substantially match the complementary arced inner surface profile of substantially circular electrode segments and ring contacts. This leads to increased surface contact between them, and accordingly, superior coupling of the surfaces and superior conductivity transfer between the conducting sections and electrode segments and ring contacts.

Figure 32:
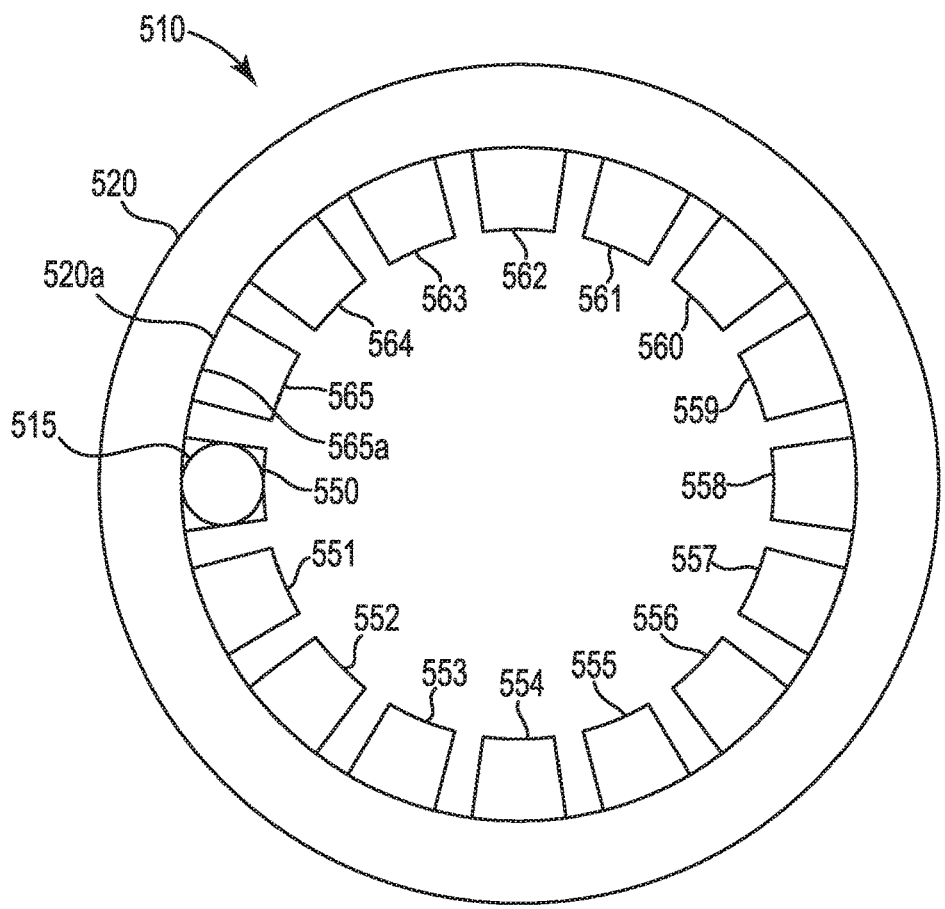
FIG. 32 illustrates a partial end view, with portions removed, of a lead body with in accordance with one embodiment.

FIG. 32 illustrates a lead body 510 in accordance with one embodiment exemplifying such a coupling of conducting sections. In one embodiment, a peripheral conductive member 520 is provided at an outer periphery of the lead body 510. In one embodiment, peripheral conductive member 520 is a ring electrode (for example, 20, 22, 24, 26) or segmented electrode (20a/b/c/d etc.), such as from lead body 10 or 210 described above. In one embodiment, peripheral conductive member 520 is a ring contact (for example, 320, 322, 324, 326, etc.), such as from lead body 310 or 410 described above.

In one embodiment, 16 conducting sections 550-565 are part of a sectioned hypotube and are provided within peripheral conductive member 520, analogous to FIG. 8B, FIG. 26 and FIG. 29 discussed above. In one embodiment, conducting sections 550-565 are formed as part of a sectioned hypotube from a cylindrical hypotube having a substantially circular outer diameter that is substantially similar to the inner diameter of peripheral conductive member 520. Accordingly, the profile of inner surface 520a of peripheral conductive member 520 matches up with the outer surface 565a of conducting section 565—they are both arcs. Each of the other conducting sections 550-564 align similarly with the profile of inner surface 520a of peripheral conductive member 520.

Figure 33A:
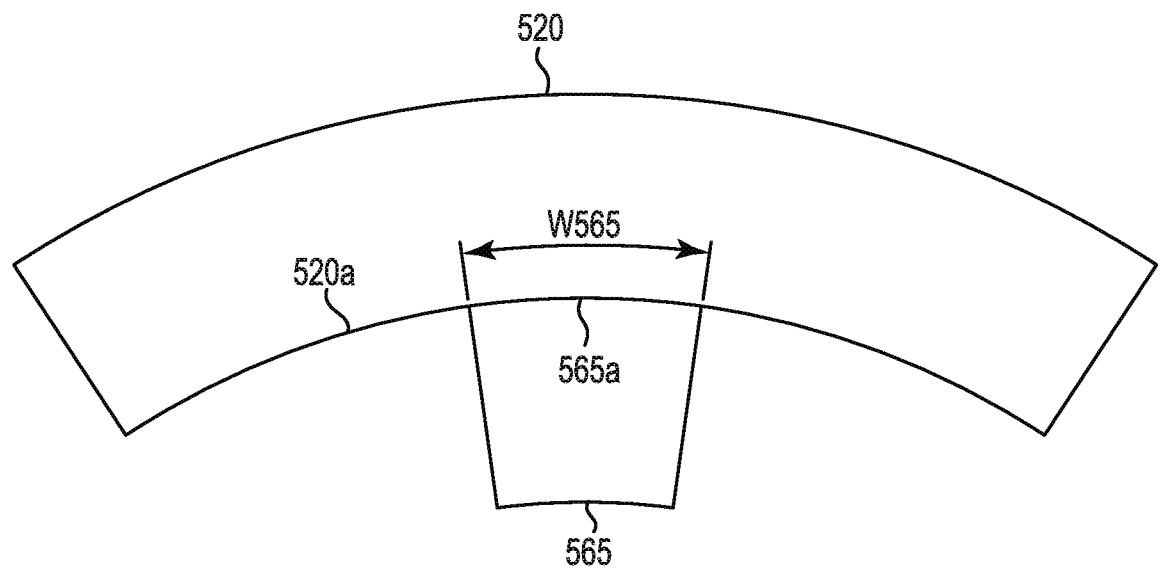
FIG. 33A illustrates a section taken from the partial end view of FIG. 32.

FIG. 33A illustrates an enlarged view of the connection of conducting section 565 to the inner surface 520a of peripheral conductive member 520. In one embodiment, when conducting sections 550-565 are formed from a cylindrical hypotube, laser cutting or similar techniques separate each of the conducting sections 550-565 into a sectioned hypotube, but do not substantially modify the outer surface of any of the conducting sections, such as outer surface 565a. As such, outer surface 565a is an arc that substantially contacts inner surface 520a, which is also an arc, across the entire width W565 of conducting section 565. Accordingly, conducting section 565 can be welded or otherwise coupled to peripheral conductive member 520 across the entire width W565 of conducting section 565, providing excellent mechanical coupling as well as excellent conductive transfer between them.

Figure 33B:
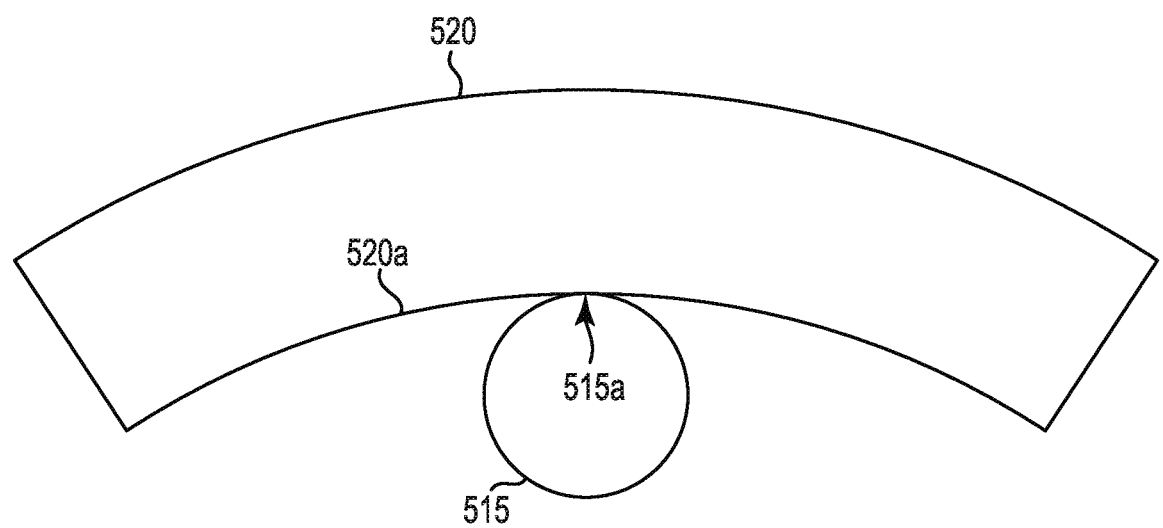
FIG. 33B illustrates a section taken from the partial end view of FIG. 32.

In contrast, FIG. 32 illustrates a conventional wire connector 515 superimposed over conducting section 550 for comparison. As illustrated in FIG. 33B, such a conventional wire connector 515 has a much smaller surface contact with the inner surface 520a of peripheral conductive member 520. In fact, where wire connector 515 is substantially round, there is only a contact point 515a between wire connector 515 and peripheral conductive member 520 in the cross-sectional view. Laser welding or otherwise connecting at this single point 515a will create an inferior mechanical and conductive connection compared with the larger surface area connection illustrated in FIG. 33A.

In one embodiment, distal portions of lead bodies, such as 10 and 210 discussed above, may be coupled to proximal portions of lead bodies, such as lead bodies 310 and 410 discussed above. Because the respective conducting sections of each such lead body are extremely small in dimensions, and each have many such conducting sections, coupling all of them can be a challenge from a manufacturing standpoint.

For example, in one embodiment, the plurality of conducting sections 30 from lead body segment 10 in FIG. 1 can be coupled to the plurality of conducting sections 340 in lead body 310 in FIG. 18. As discussed above, in one embodiment, lead body segment 10 has a plurality of segmented electrodes 20-26 carried about the perimeter of lead body segment 10 near an end 12. In one embodiment, end 12 is the distal end that is typically placed in contact with tissue within a body that is to be either sensed or stimulated. The segmented electrodes 20-26 either transmit energy to, or receive energy from, the tissue. Conducting sections 30 are then coupled to further portions of a lead body segment, such as the plurality of conducting sections 340 in lead body 310 in FIG. 18. These plurality of conducting sections 340 are respectively coupled to ring contacts that are then coupled back to a generator or implantable device. In embodiments where many segmented electrodes are used, such as 8 or 16 or more electrodes, there are typically an equal number of conducting sections that must be coupled back to a generator. In some embodiments, the outer diameter of lead body segment 10 is quite small, for example less than 0.100 inches or even less than 0.031 inches.

Figure 34A:
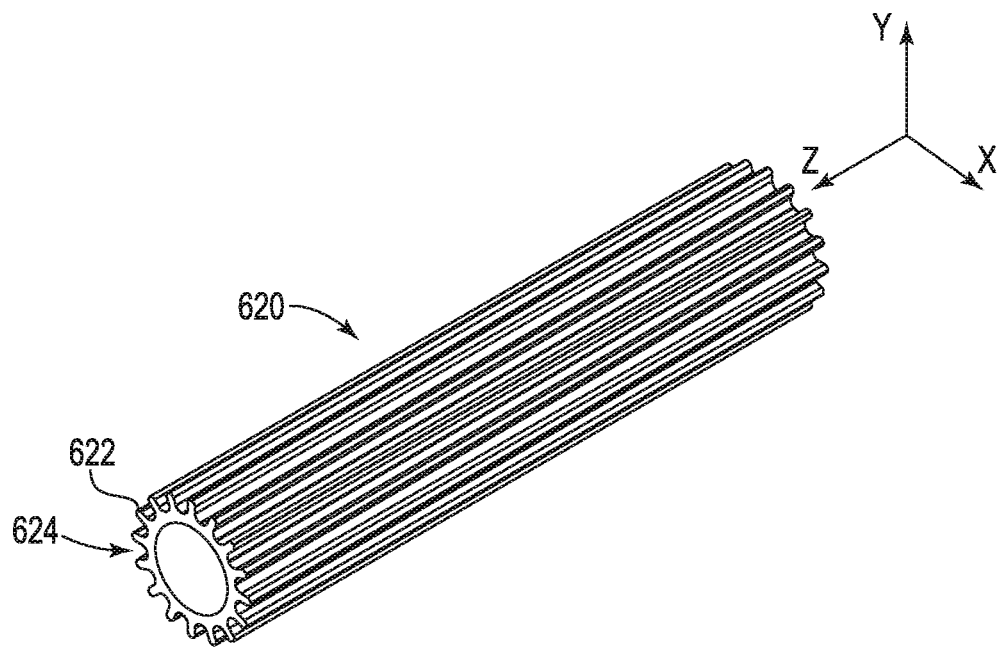
FIGS. 34A and 34B illustrate perspective and end views of a strain relief coupler in accordance with one embodiment.
Figure 34B:
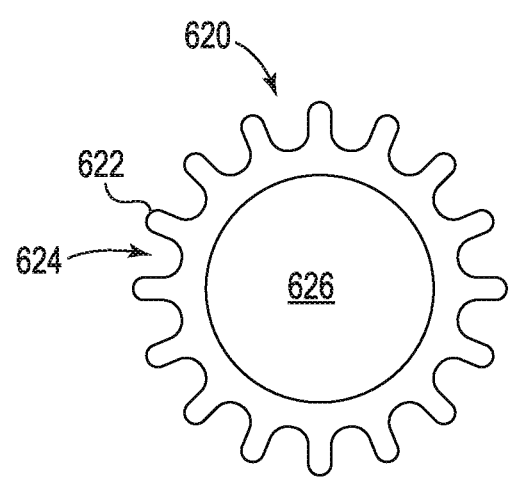

FIGS. 34A-34B illustrate strain relief coupler 620 in accordance with one embodiment, which may be used to couple the plurality of conducting sections 30 from lead body segment 10 in FIG. 1 to the plurality of conducting sections 340 in lead body 310 in FIG. 18.

In one embodiment, strain relief coupler 620 has an axial length (in the z-axis direction of FIG. 34A) and has a plurality of tines 622 projecting radially outward along the axial length of coupler 620. Between each of the radially-projecting tines 622, channels 624 are defined that also extend along the axial length of coupler 620. The number of tines 622 and number of channels 624 can be adjusted for any particular application. In the embodiment of FIGS.

34A-34B, sixteen tines 622 and sixteen respective channels 624 are illustrated between the tines 622. In one embodiment, strain relief coupler 620 defines an inner lumen 626. As will be explained below, inner lumen 626 can be maintained to define the inner lumen of a lead body 10.

Figure 35A:
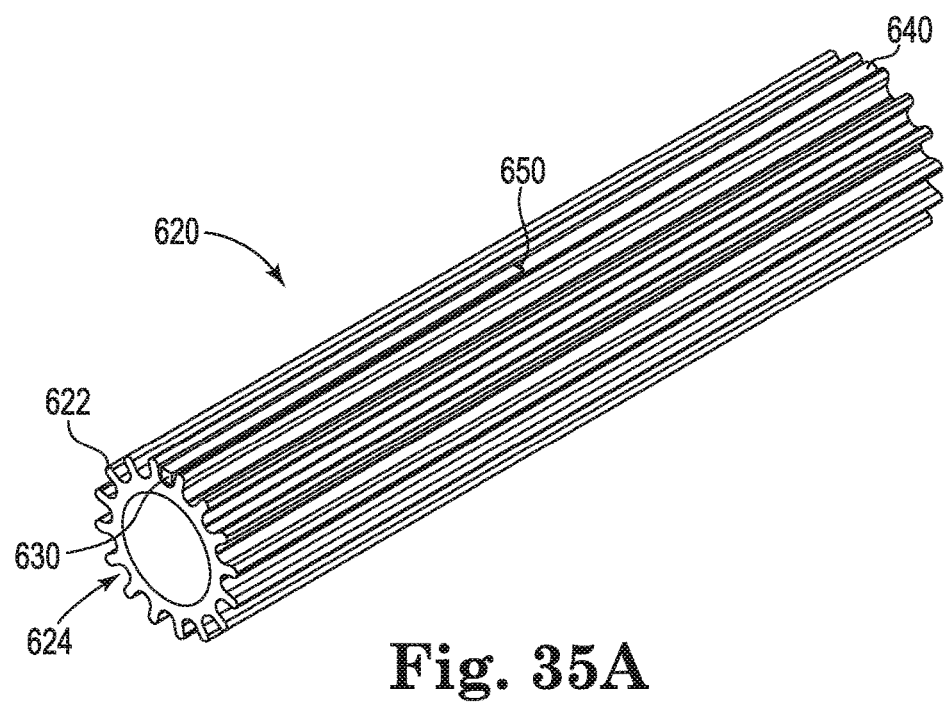
FIGS. 35A and 35B illustrate perspective and side views of a strain relief coupler carrying wires to be joined in accordance with one embodiment.
Figure 35B:
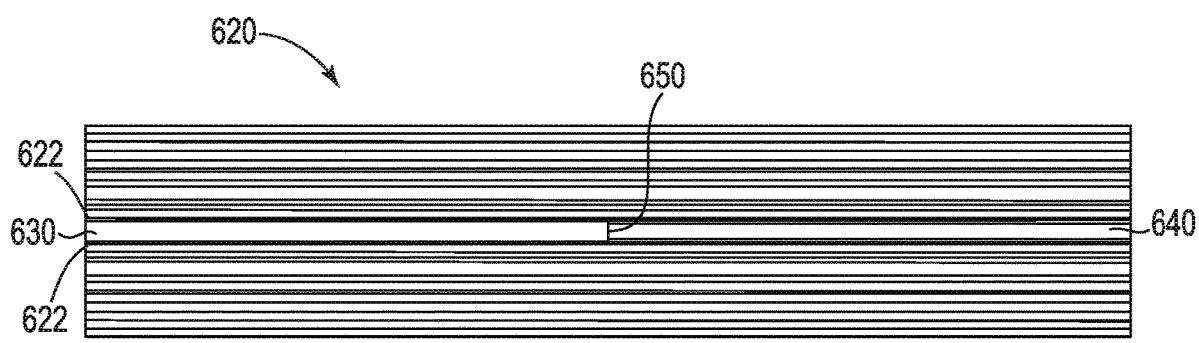

FIGS. 35A-35B illustrate strain relief coupler 620 with first and second conducting sections 630, 640 in accordance with one embodiment. In one embodiment, strain relief coupler 620 is used to couple two sets of conducting sections, such as conducting sections 30 from lead body segment 10 in FIG. 1 to the plurality of conducting sections 340 in lead body 310 in FIG. 18.

In one embodiment, a first conducting section 630, from a first set of conducting sections is placed in a channel 624 of strain relief coupler 620 on one side. In the illustration of FIG. 35B, first conducting section 630 is one the left side. A second conducting section 640 from a second set of conducting sections is placed in a channel 624 of strain relief coupler 620 on the opposite side of the first conducting section 630, and placed in the same channel 624. In the illustration of FIG. 35B, second conducting section 640 is one the right side. The respective ends of first and second conducting sections 630, 640 are butted up against each other at joint 650. For simplification of illustration, only first and second conducting sections 630, 640 are shown, but in one embodiment, each of the remaining channels 624 are likewise filled with conducting sections from the two respective sets of conducting sections, conducting sections from the first set on the left side and conducting sections from the second set on the right side. Also in the figure, conducting sections 630, 640 are illustrated as square-shaped conductors, but conducting sections can be any of a variety of conducting materials and wires and may have any of a multitude of cross-sectional shapes, such as rectangular, round, oval, etc.

Figure 36A:
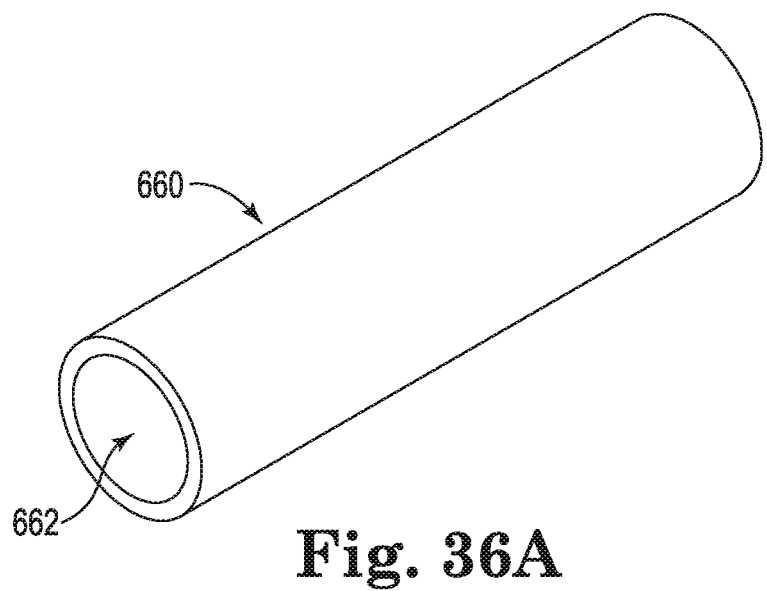
FIGS. 36A and 36B illustrate perspective and end views of a holding sleeve in accordance with one embodiment.
Figure 36B:
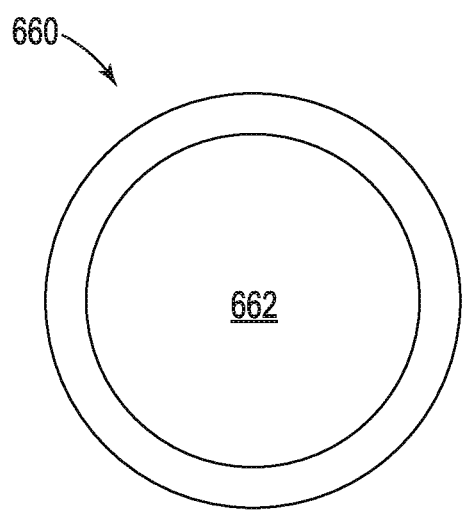

In one embodiment, once the conducting sections 630, 640 are placed in the channels 624, retaining sleeve 660, illustrated in FIG. 36A-36B is then placed over strain relief coupler 620. In one embodiment, retaining sleeve 660 has an opening 662 with a diameter that is configured to accommodate strain relief coupler 620, such that the diameter of opening 662 is approximately the same as a diameter formed by the outer radial dimensions of tines 622. In this way, once retaining sleeve 660 is placed over strain relief coupler 620, any conducting sections within channels 624 are secured between tines 622 and sleeve 660. In one embodiment, two sleeves 660 are placed over each end of the strain relief coupler 620, such that a first sleeve 660 retains a first set of conducting sections on one side and a second sleeve 660 retains a second set of conducting sections on the opposite side.

Figure 37:
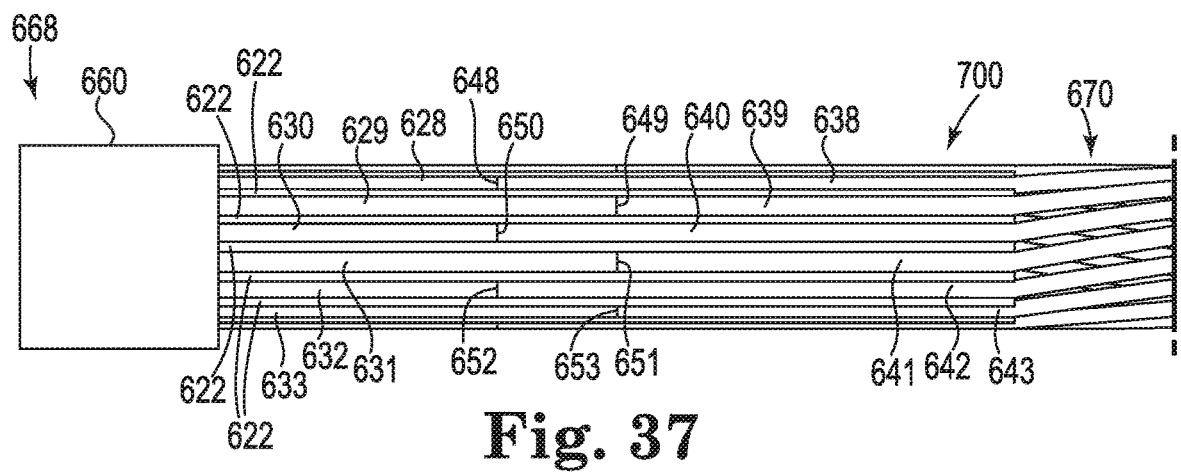
FIG. 37 illustrates a partial view of a joined lead body with a strain relief coupler, conducting wires and a holding sleeve in accordance with one embodiment.

FIG. 37 illustrates a partially assembled lead body 700 in accordance with one embodiment. Lead body 700 includes strain relief coupler 620, a first set of conducting sections 628-633, a second set of conducting sections 638-643, and retaining sleeve 660. In one embodiment, strain relief coupler 620 is used to couple a first portion 668 of lead body 700 to a second portion 670 of a lead body 700. In order to couple the first and second portions 668, 670 of lead body 700 together, a first set of conducting sections 628-633 from the first portion 668 are placed in the channels of strain relief coupler 620 on one side, and a second set of conducting sections 638-643 from the second portion 670 are placed in the channels 624 of strain relief coupler 620 on the other side. Ends of each of conducting sections 628-633 of the first set are placed against respective ends of each of conducting sections 638-643 from the second set at joints 648-653.

Because each of the conducting sections are secured between tines 622 and within channels 624, they can be readily welded together at joints 648-653, yet kept electrically insulated from adjacent wires by tines 622. In one embodiment, joints 648-653 are staggered or offset relative to each other so that the welding of one joint will not adversely affect an adjacent joint. For example, in the illustration of FIG. 37, welding conducting section 630 to conducting section 640 at joint 650 will not adversely affect joints 649 or 651, because these adjacent joints are axially offset (to the right as illustrated in the figure) relative to joint 650. The joints 648-653 can be laser welded, soldered, brazed, glued or coupled in any of a variety of ways.

In the illustration, six conducting sections 628-633 of the first set and six conducting sections 638-643 of the second set are visible in FIG. 37, but because strain relief coupler 620 is substantially circular in cross-section, more conductors are contained on non-visible portions of the figure on the other side. The number of channels 624 of coupler 620 can be varied to accommodate the number of conducting sections that are to be coupled, for example, four, eight, sixteen or more conducting sections can be joined.

In one embodiment, the first portion 668 of lead body 700 that is coupled to the second portion 670 of lead body 700 is a lead body with electrodes, such as illustrated in FIG. 1. Each electrode in the electrode array is coupled to only one conducting section that is then coupled within one channel 624 of coupler 620. In one embodiment, the second portion 670 of lead body 700 that is coupled to the first portion 668 of lead body 700 is a lead body with proximal ring contacts, such as illustrated in FIG. 18. Each ring contact of the proximal contacts is coupled to only one conducting section that is then coupled within one channel 624 of coupler 620. In each case, the coupled conducting section is then joined to the remaining conducting section to form the completed lead body 700.

Figure 38:
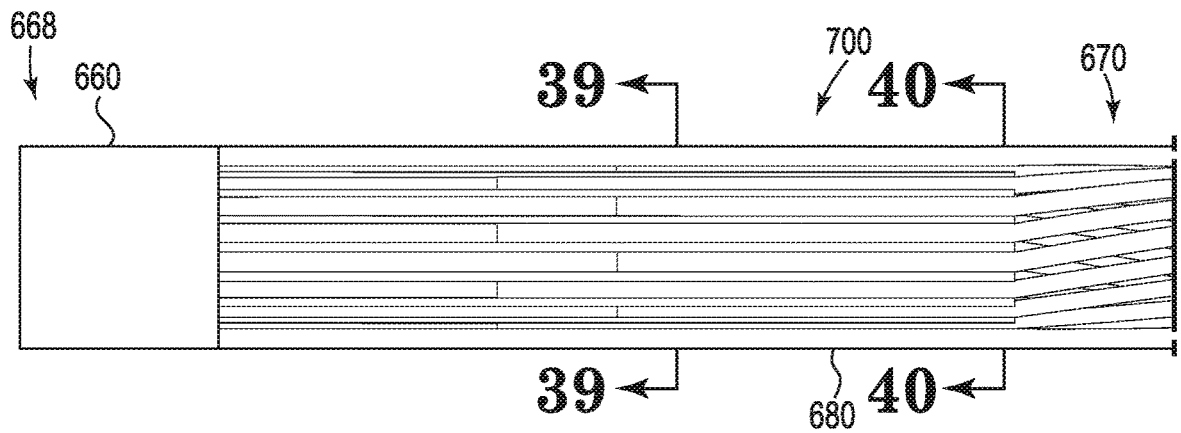
FIG. 38 illustrates a joined lead body with a strain relief coupler, conducting wires and a holding sleeve in accordance with one embodiment.

FIG. 38 illustrates lead body 700 with strain relief coupler 620 in accordance with one embodiment. After the conducting sections of first and second portions 668, 670 are joined as described with respect to FIG. 37 above, outer layer 680 is formed over the conducting sections and coupler 620 in order to form the finished lead body 700. In FIG. 38 outer layer 680 is partially ghosted so that conducting sections, which were previously described with respect to FIG. 37, are visible beneath the layer 680. In one embodiment, the partially assembled lead body 700 in FIG. 37 is placed in an injection mold (such as illustrated in FIGS. 6 and 24) and outer layer 680 is formed by injecting a polymer material over the assembly, which forms the final outer diameter of lead body 700.

In one embodiment, sleeve 660 is left on the partially assembled lead body 700 of FIG. 37 when it is placed in the injection mold. As such, when the polymer material that forms outer layer 680 is injected into the mold cavity during the injection molding process, the heated flowing polymer material also causes sleeve 660 to at least partially reflow as well. In one embodiment, the outer diameter of sleeve 660 will be matched to that of outer layer 680 so that the final lead body 700 has a smooth and uniform outer diameter. In other embodiments, a sleeve 660 is left on both sides of joints 648-653 such that outer layer 680 is flowed over coupler 620 and the conducting sections between the sleeves 660 to form the final outer dimensions of lead body 700. In yet other embodiments, sleeves 660 are either not used or are removed from the assembly before it is placed in the mold cavity such that polymer material is flowed over the entire lead assembly and forms the final over layer 680.

In one embodiment, coupler 620 is a polymer material, as is outer layer 680. In this way, when the polymer material that forms outer layer 680 is injected into the mold cavity during the injection molding process, the heated flowing polymer material causes coupler 620 to at least partially reflow as well. As such, the conducting sections become embedded in the combination of coupler 620 and outer layer 680 such that they are both electrically isolated and also are physically supported. In some uses of lead body 700, the conductors may be subjected to some bending and twisting as lead body 700 is pushed or pulled through the tortious intravenous or similar system. Because they are well-supported in the flowed material of the coupler 620 and outer layer 680, they will be subjected to less strain and less likely to fatigue.

Figure 39:
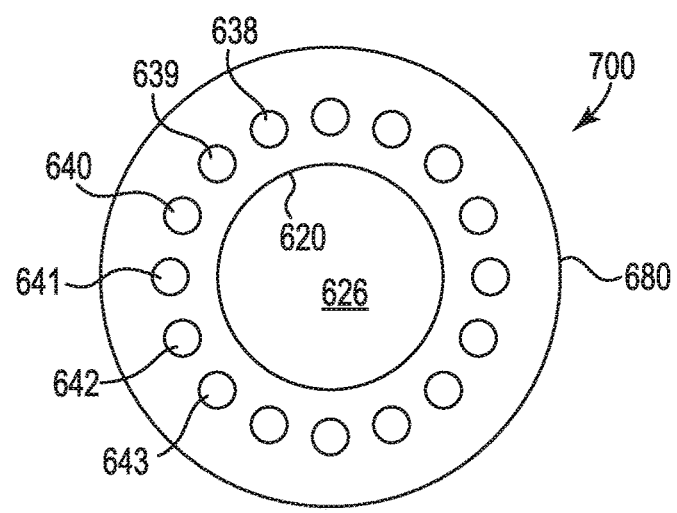
FIG. 39 illustrates a sectional view of a joined lead body with a strain relief coupler and conducting wires in accordance with one embodiment.
Figure 40:
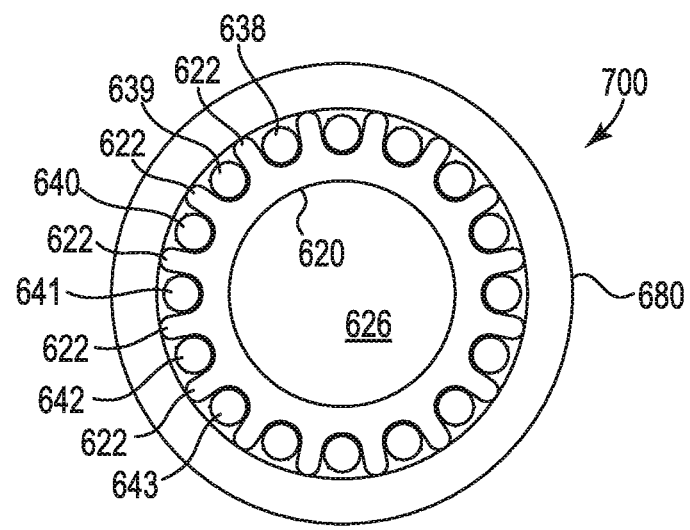
FIG. 40 illustrates a sectional view of a joined lead body with a strain relief coupler and conducting wires in accordance with one embodiment.

FIGS. 39 and 40 show respective cross-sectional views of lead body 700 taken at lines 39-39 and 40-40 on FIG. 38. In one embodiment, the injection molding process is accomplished by flowing material from the left to the right, as viewed in FIG. 38. As such, a reflowing of the polymer material used for coupler 620 occurs adjacent the joints 648-653 and continues slightly to the right of them. Accordingly, FIG. 39 illustrates how the outer layer 680 and coupler 620 have reflowed together, essentially embedding conducting sections 638-643 within the re-flowed material.

Once outer layer 680 and coupler 620 material have reflowed together, the conducting sections 628-633 of the first set, the conducting sections 638-643 of the second set, and the joints 648-653 that coupled them are all surrounded and supported by the material. As such, lead body 700 is capable of being bent, curled, pulled and pushed without jeopardizing joints 648-653, and without risk of separating the first and second portions 668, 670 of lead body 700.

FIG. 40 illustrates an area further along the axial length of lead body 700 from the source of the flowed material in one embodiment. Accordingly, in this area there is not as much reflow, or even no reflow of coupler 620. As such, the tines 622 remain intact within outer layer 680 with the various conducting sections 638-643 secured between them. In both FIGS. 39 and 40, the conducting sections that were not visible in the prior side view illustrations are visible, but are unlabeled for ease of illustration. In both embodiments, 16 conducting sections are illustrated, but other quantities of conducting sections are readily accommodated, for example, 4, 8 or 32.

In FIGS. 39 and 40, it is also illustrated that the inner diameter of coupler 620 is retained such that inner lumen 626 is available within lead body 700 for accepting guidewires or other wires and tools that can be fed within lead body 700 that can be helpful in placement, providing sensing and delivery signals or any of a variety of related applications.

Although outer layer 680 is described in one embodiment as an overmolded layer over the first and second set of conducting sections 628-633 and 638-643 and coupler 620, other means of forming outer layer 680 are used in other embodiments. For example, in one embodiment, outer layer 680 is glue that is applied over the conducting sections and coupler 620. In another embodiment, outer layer 680 is formed using a plurality of sleeves 660 that are placed over the conducting sections and coupler 620 and abutted up against one another. In one embodiment, the sleeves 660 can be glued into place. In another embodiment, sleeves can be reflowed once in place to form outer layer 680. Other combinations of these various embodiments are also possible.

Figure 41:
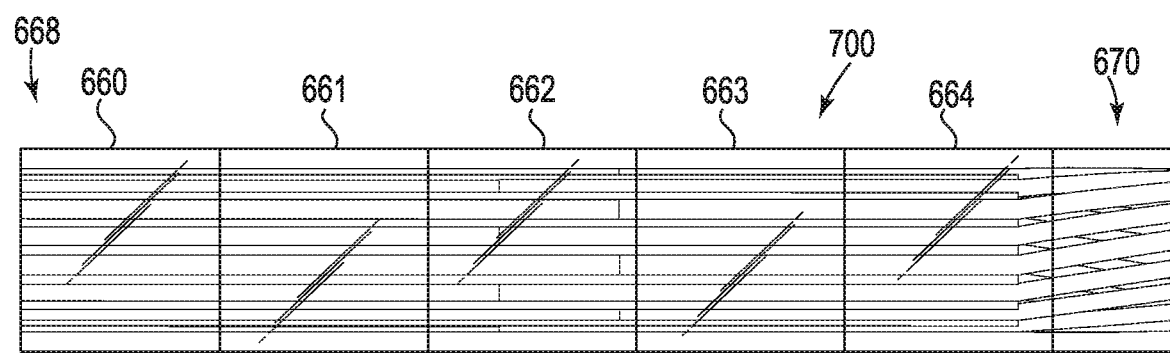
FIG. 41 illustrates a joined lead body with a strain relief coupler, conducting wires and holding sleeves in accordance with one embodiment.

FIG. 41 illustrates lead body 700 with strain relief coupler 620 in accordance with one embodiment. After the conducting sections of first and second portions 668, 670 are joined as described with respect to FIG. 37 above, a plurality of sleeves 660, 661, 662, 663, 664 are placed over the conducting sections and coupler 620 in order to form the finished lead body 700. In FIG. 41, each of sleeves 660, 661, 662, 663, 664 are partially ghosted so that conducting sections, which were previously described with respect to FIG. 37, are visible beneath the layer. In one embodiment, sleeves 660, 661, 662, 663, 664 are glued over conducting sections and coupler 620 to form lead body 700. In another embodiments, once sleeves 660, 661, 662, 663, 664 are in place, they are heated to re-flow the material of sleeves 660, 661, 662, 663, 664 so that each of the sleeves melt together to form a uniform cover over conducting sections and coupler 620.

Lead body 700, using strain relief coupler 720, allows coupling of conducting sections and wire conductors having small sizes that were prohibitively small with prior configurations of lead bodies. Because strain relief coupler 620 secures conducting sections within its channels 624, such that one set of conducting sections can be secure to another, very small size diameter wires can be joined with this configuration. For example, in various embodiments, conducting sections having outer diameters (OD) as small as 0.001 inches can be coupled using strain relief coupler 620.

Accordingly, because such tiny conductors can be effectively joined and then fully secured within strain relief coupler 620 of lead body 700, even during use, the number of conductors that can be included within lead body 700 can be increased over previous configurations. In the embodiments illustrated in figures, as many as 16 conducting sections can be included within lead body 700. Also because of the small OD of the conducting sections, a relatively small OD for lead body 700 is also achievable despite the large number of conducting sections.

In one embodiment, the number of conducting sections that can be included within lead body 700 is a function of the OD of each of the conducting sections. In various embodiments, the following Table 3 illustrates achievable conducting section OD with associated achievable lead body 700 OD and overall number of conducting sections:

TABLE 3

| | | Achievable Lead Diameter | |
|---|---|---|---|
| | | 8 Channel | 16 Channel |
| Conducting Section OD (in) | .001" | .021" | .031" |
| | .003" | .031" | .051" |
| | .005" | .041" | .064" |
| | .010" | .064" | .103" |

As illustrated, when coupling sets of conducting sections within the channels of a strain relief coupler that have an OD of 0.001 inches, as many as 8 overall conducting sections can be included within a lead body that has an OD of 0.021 inches, and as many as 16 overall conducting sections can be included within a lead body that has an OD of 0.031 inches. Such sizes and number of conducting sections were not achievable with prior known assembly techniques and lead configurations. Facilitating such a large number of conducting sections in such small OD lead bodies allows lead body 700 to be used in applications where 8, 16, 32 or even more independent conducting sections are needed in very small diameter package.

Although specific embodiments have been illustrated and described herein, it will be appreciated by those of ordinary skill in the art that a variety of alternate and/or equivalent implementations may be substituted for the specific embodiments shown and described without departing from the scope of the invention. This application is intended to cover any adaptations or variations of the specific embodiments discussed herein. Therefore, it is intended that this invention be limited only by the claims and the equivalents thereof.

What is claimed is:

1. A lead body for medical implantation comprising:
a first set of conducting sections;
a second set of conducting sections;
a strain relief coupler having an axial length with a plurality of tines extending along the axial length and extending radially thereby defining a plurality of axially-extending channels;
a plurality of joints located within the plurality of channels, each joint coupling one conducting section from the first set of conducting sections to one conducting section from the second set of conducting sections; and
an outer layer at least partially surrounding the first and second set of conducting sections, the plurality of joints and the strain relief coupler; and
a first sleeve attached over the first set of conducting sections and over the strain relief coupler and the first sleeve configured to securely hold the first set of conducting sections against the strain relief coupler on a first side of the plurality of joints and a second sleeve attached over the second set of conducting sections and over the strain relief coupler and the second sleeve configured to securely hold the second set of conducting sections securely against the strain relief coupler on a second side of the plurality of joints, which is opposite the first side, and wherein the first and second sleeves are spaced apart to allow access to the plurality of joints.

2. The lead body of claim 1, wherein the plurality of joints are all offset such that no two joint of the plurality of joints are immediately adjacent each other.

3. The lead body of claim 1, wherein the conducting sections all have either a substantially circular shaped cross-section or a substantially square shaped cross-section and wherein the conducting sections all have an outer diameter between 0.001 inches and 0.010 inches.

4. The lead body of claim 1, wherein the outer diameter of the lead body is between 0.021 inches and 0.103 inches.

5. The lead body of claim 1, wherein the outer layer is a polymer material that is flowed over the conducting sections and strain relief coupler.

6. The lead body of claim 1, wherein the router layer comprises a polymer material that is at least partially re-flowed when the outer layer is formed over the conducting sections and strain relief coupler.

7. The lead body of claim 1, wherein at least one of the plurality of joints comprises one of a laser welding, a solder, an adhesive and a braze.

8. The lead body of claim 1, wherein the first and second sets of conducting sections each comprise 4, 8, or 16 individual conducting sections.

9. The lead body of claim 1, wherein the plurality of tines of the strain relief coupler have a collective outer radial dimension, and wherein the first and second sleeves each are configured with an opening having a diameter that is approximately the same as a diameter formed by the collective outer radial dimension of the plurality of tines of the strain relief coupler.

* * * * *